(12) United States Patent
Pleshko et al.

(10) Patent No.: US 12,629,013 B2
(45) Date of Patent: May 19, 2026

(54) ARTHROSCOPIC PROBE DEVICE, SYSTEM AND METHOD

(71) Applicant: Temple University-Of The Commonwealth System Of Higher Education, Philadelphia, PA (US)

(72) Inventors: Nancy Pleshko, Cherry Hill, NJ (US); Shital Kandel, Philadelphia, PA (US); Jessica M. Falcon, New York, NY (US); William Querido-Maciel, Philadelphia, PA (US); Jack Oswald, Melrose Park, PA (US)

(73) Assignee: Temple University-Of The Commonwealth System Of Higher Education, Philadelphia, PA (US)

( * ) Notice: Subject to any disclaimer, the term of this patent is extended or adjusted under 35 U.S.C. 154(b) by 461 days.

(21) Appl. No.: 18/175,854

(22) Filed: Feb. 28, 2023

(65) Prior Publication Data

US 2023/0277052 A1     Sep. 7, 2023

Related U.S. Application Data

(60) Provisional application No. 63/315,362, filed on Mar. 1, 2022.

(51) Int. Cl.
| | |
|---|---|
| *A61B 1/317* | (2006.01) |
| *A61B 1/00* | (2006.01) |
| *A61B 1/07* | (2006.01) |

(52) U.S. Cl.
CPC .......... *A61B 1/317* (2013.01); *A61B 1/00096* (2013.01); *A61B 1/07* (2013.01)

(58) Field of Classification Search
CPC ....... A61B 1/317; A61B 1/00096; A61B 1/07; A61B 1/00165
See application file for complete search history.

(56) References Cited

U.S. PATENT DOCUMENTS

| | | | |
|---|---|---|---|
| 5,219,345 A * | 6/1993 | Potter ................. | A61B 5/0084 356/73.1 |
| 5,512,034 A * | 4/1996 | Finn ................... | A61B 1/00135 600/138 |

(Continued)

FOREIGN PATENT DOCUMENTS

WO      WO-2004111700 A1 *  12/2004  .......... A61B 5/0062

OTHER PUBLICATIONS

Examination of SMA Connector Parameters (Year: 2012).*

(Continued)

*Primary Examiner* — Anh T Nguyen
*Assistant Examiner* — Shankar Raj Ghimire
(74) *Attorney, Agent, or Firm* — Riverside Law LLP

(57) ABSTRACT

An arthroscopic probe system comprises a spectrometer, a computing system connected to the spectrometer and an arthroscopic probe device comprising a probe shaft including a proximal end and probe tip positioned at a distal end, a handle including a proximal end and a distal end, wherein the distal end of the handle is connected to the proximal end of the probe shaft, a cable including a first end and a second end, wherein the first end is connected to the proximal end of the handle, and at least one optical fiber, wherein a first end of the at least one optical fiber is optically connected to the probe tip, wherein the at least one optical fiber is positioned internally to the probe shaft, handle and cable, and wherein a second end of the at least one optical fiber terminates at the second end of the cable.

15 Claims, 19 Drawing Sheets

(56)                    References Cited

U.S. PATENT DOCUMENTS

| | | | | |
|---|---|---|---|---|
| 5,554,100 | A * | 9/1996 | Leiner | A61B 1/07 |
| | | | | 600/920 |
| 5,735,792 | A * | 4/1998 | Vanden Hoek | A61B 1/042 |
| | | | | 600/138 |
| 6,152,872 | A * | 11/2000 | Peck | A61B 1/0623 |
| | | | | 359/435 |
| 7,322,962 | B2 * | 1/2008 | Forrest | A61F 2/442 |
| | | | | 604/164.01 |
| 8,075,478 | B2 * | 12/2011 | Campos | A61B 1/00165 |
| | | | | 600/129 |
| 8,123,678 | B2 * | 2/2012 | Lawrence | A61B 1/012 |
| | | | | 600/151 |
| 8,721,327 | B2 * | 5/2014 | Karazivan | A61B 5/4547 |
| | | | | 433/29 |
| 9,005,115 | B2 * | 4/2015 | Vayser | A61B 1/00135 |
| | | | | 606/17 |
| 9,629,528 | B2 * | 4/2017 | Woods | A61B 1/0661 |
| 10,595,710 | B2 * | 3/2020 | Gill | A61B 1/00135 |
| 11,147,432 | B2 * | 10/2021 | Hirono | A61B 1/00121 |
| 11,490,797 | B2 * | 11/2022 | Gora | A61B 1/0002 |
| 11,497,382 | B1 * | 11/2022 | Ikuta | A61B 1/00096 |
| 12,279,748 | B2 * | 4/2025 | Lu | A61B 1/00042 |
| 2002/0013513 | A1 * | 1/2002 | Bala | A61B 1/042 |
| | | | | 600/178 |
| 2003/0163178 | A1 * | 8/2003 | Davison | A61B 18/148 |
| | | | | 607/101 |
| 2004/0215184 | A1 * | 10/2004 | Eggers | A61B 18/1206 |
| | | | | 606/41 |
| 2005/0234298 | A1 * | 10/2005 | Kucklick | A61B 17/0218 |
| | | | | 600/156 |
| 2008/0064925 | A1 * | 3/2008 | Gill | A61B 1/00167 |
| | | | | 600/109 |
| 2010/0228123 | A1 * | 9/2010 | Brennan | A61B 3/10 |
| | | | | 606/41 |
| 2014/0235942 | A1 * | 8/2014 | Hellstrom | A61B 1/0615 |
| | | | | 128/200.26 |
| 2015/0087912 | A1 * | 3/2015 | Vogel | A61B 1/00183 |
| | | | | 600/176 |
| 2018/0049761 | A1 * | 2/2018 | Bashir | A61B 18/00 |
| 2019/0033506 | A1 * | 1/2019 | Weber | A61B 1/00167 |
| 2019/0223706 | A1 * | 7/2019 | Takeuchi | A61B 1/07 |
| 2025/0194904 | A1 * | 6/2025 | Tilson | A61B 1/00135 |

OTHER PUBLICATIONS

Bonasia, Davide Edoardo, et al. "Intra-and inter-observer reliability of ten major histological scoring systems used for the evaluation of in vivo cartilage repair." Knee Surgery, Sports Traumatology, Arthroscopy 23.9 (2015): 2484-2493.

Hofmann GO, Marticke J, Grossstuck R, Hoffmann M, Lange M, Plettenberg HK, Braunschweig R, Schilling O, Kaden I, Spahn G. Detection and evaluation of initial cartilage pathology in man: A comparison between MRT, arthroscopy and near-infrared spectroscopy (NIR) in their relation to initial knee pain. Pathophysiology. Feb. 2010;17(1):1-8.

Jungmann, Pia M., et al. "Magnetic resonance imaging score and classification system (AMADEUS) for assessment of preoperative cartilage defect severity." Cartilage 8.3 (2017): 272-282.

Marticke JK, Hosselbarth A, Hoffmeier KL, Marintschev I, Otto S, Lange M, Plettenberg HK, Spahn G, Hofmann GO. How do visual, spectroscopic and biomechanical changes of cartilage correlate in osteoarthritic knee joints? Clin Biomech (Bristol, Avon). May 2010;25(4):332-40.

McGoverin, Cushla M., et al. "Nondestructive assessment of engineered cartilage composition by near infrared spectroscopy." Annals of biomedical engineering 44.3 (2016): 680-692.

Querido, William, et al. "Vibrational spectroscopy and imaging: applications for tissue engineering." Analyst 142.21 (2017): 4005-4017.

Roos, Ewa M., et al. "ICRS recommendation document: patient-reported outcome instruments for use in patients with articular cartilage defects." Cartilage 2.2 (2011): 122-136.

Sarin JK, Te Moller NC, Mancini IA, Brommer H, Visser J, Malda J, van Weeren PR, Afara IO, Toyras J. Arthroscopic near infrared spectroscopy enables simultaneous quantitative evaluation of articular cartilage and subchondral bone in vivo. Scientific reports. Sep. 7, 2018;8(1):1-0.

Spahn G, Klinger HM, Baums M, Hoffmann M, Plettenberg H, Kroker A, Hofmann GO. Near-infrared spectroscopy for arthroscopic evaluation of cartilage lesions: results of a blinded, prospective, interobserver study. Am J Sports Med. Dec. 2010;38(12):2516-21.

Spahn G, Plettenberg H, Hoffmann M, Klemm HT, Brochhausen-Delius C, Hofmann GO. The frequency of cartilage lesions in non-injured knees with symptomatic meniscus tears: results from an arthroscopic and NIR—(near-infrared) spectroscopic investigation. Arch Orthop Trauma Surg. Jun. 2017;137(6):837-844.

Spahn G, Plettenberg H, Kahl E, Klinger HM, Mückley T, Hofmann GO. Near-infrared (NIR) spectroscopy. A new method for arthroscopic evaluation of low grade degenerated cartilage lesions. Results of a pilot study. BMC Musculoskelet Disord. May 29, 2007; 8:47.

Spahn G, Plettenberg H, Nagel H, Kahl E, Klinger HM, Mückley T, Günther M, Hofmann GO, Mollenhauer JA. Evaluation of cartilage defects with near-infrared spectroscopy (NIR): an ex vivo study. Med Eng Phys. Apr. 2008;30(3):285-92.

Stumpfe ST, Pester JK, Steinert S, Marintschev I, Plettenberg H, Aurich M, Hofmann GO. Is there a correlation between biophotonical, biochemical, histological, and visual changes in the cartilage of osteoarthritic knee-joints? Muscles Ligaments Tendons J. Aug. 11, 2013;3(3):157-65.

Yousefi, Farzad, et al. "Near-infrared spectroscopy predicts compositional and mechanical properties of hyaluronic acid-based engineered cartilage constructs." Tissue Engineering Part A 24.1-2 (2018): 106-116.

* cited by examiner

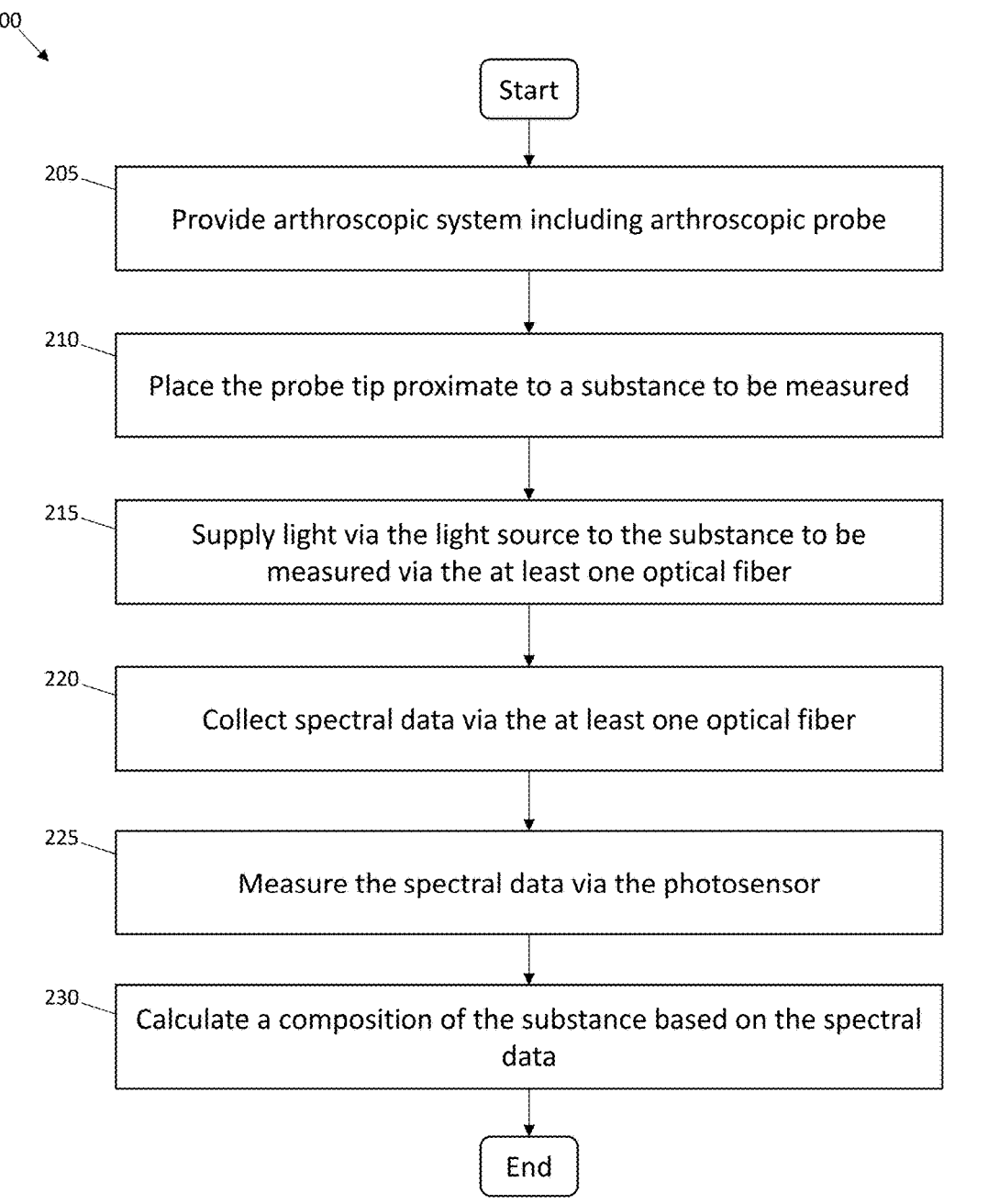

200

205 — Provide arthroscopic system including arthroscopic probe

210 — Place the probe tip proximate to a substance to be measured

215 — Supply light via the light source to the substance to be measured via the at least one optical fiber 220 — Collect spectral data via the at least one optical fiber 225 — Measure the spectral data via the photosensor 230 — Calculate a composition of the substance based on the spectral data

FIG. 8

ARTHROSCOPIC PROBE DEVICE, SYSTEM AND METHOD

CROSS-REFERENCE TO RELATED APPLICATIONS

This application claims priority to U.S. provisional application No. 63/315,362 filed on Mar. 1, 2022, incorporated herein by reference in its entirety.

STATEMENT REGARDING FEDERALLY SPONSORED RESEARCH OR DEVELOPMENT

This invention was made with government support under R01 AR056145 awarded by the National Institutes of Health. The government has certain rights in the invention.

BACKGROUND OF THE INVENTION

Arthroscopy is a routine surgical procedure used to assess joint health. The increasing prevalence of joint disorders and injuries coupled with the growing demand for minimally invasive surgeries is anticipated to drive a fast growth in the global arthroscopy device market over the next 5-10 years. With the development in technology and improvements to traditional devices, the arthroscopic procedure volume is also expected to substantially rise.

In the search for a non-destructive minimally invasive technique for the objective assessment of cartilage, infrared-based methods have been established over the last 15-20 years. Infrared spectroscopy is based on absorbance of infrared light by tissue functional groups at specific vibrational frequencies, and thus, it is dependent on properties of the analyzed sample, yielding very objective and reliable results. In particular, near infrared (NIR) spectroscopy is a non-destructive and non-harmful technique widely used to evaluate the composition of various biological tissues, including joint cartilage, tendons and bones. Moreover, NIR has a large depth of penetration from millimeters to centimeters, allowing users to probe entire tissue depths. NIR is a well-established and non-harmful light technology that is currently used in several FDA-approved medical devices aiding in a favorable market acceptance. For example, the Infrascanner Model 2000 was approved in 2013 (510(k) #K120949).

Joint lesions are very common and can be debilitating if not diagnosed and treated properly. The most commonly used surgical technique to diagnose and treat joint injury or degradation is an arthroscopic intervention. Arthroscopy is the procedure in which surgeons create a small incision in the skin and insert a camera for visualization of the joint. In addition to cameras, other arthroscopy instruments are inserted into a secondary port for use by the surgeon. Specifically, the arthroscopic hook probe and retractor is the most common device used, allowing the surgeon to examine joint quality by mechanically probing the cartilage surface.

Based on palpation and visual aspects, the surgeon assesses cartilage quality using score systems such as the International Cartilage Repair Society (ICRS) score, the Oswestry arthroscopy score and the O'Driscoll score for regenerative cartilage repair, and the Outerbridge score for joint cartilage breakdown, among other macroscopic evaluation systems.

However, assessment of cartilage properties using these scoring systems is limited to surgeon subjectivity, relying mostly on surgeon perception of the "feel" of the tissue by the probe tip. Therefore, there is an urgent need for a technology that moves assessment from a subjective assessment to an objective quantifiable system.

SUMMARY OF THE INVENTION

Some embodiments of the invention disclosed herein are set forth below, and any combination of these embodiments (or portions thereof) may be made to define another embodiment.

In one aspect, an arthroscopic probe device comprises a probe shaft including a proximal end and probe tip positioned at a distal end, wherein the probe tip includes a bent portion at an angle in the range of about 50 to 150 degrees in relation to a central longitudinal axis of the probe shaft, a handle including a proximal end and a distal end, wherein the distal end of the handle is connected to the proximal end of the probe shaft, a cable including a first end and a second end, wherein the first end is connected to the proximal end of the handle, and at least one optical fiber, wherein a first end of the at least one optical fiber is optically connected to the probe tip, wherein the at least one optical fiber is positioned internally to the probe shaft, handle and cable, and wherein a second end of the at least one optical fiber terminates at the second end of the cable.

In one embodiment, the probe shaft is tapered from the proximal end to the distal end. In one embodiment, the at least one optical fiber comprises six illumination optical fibers and one collection optical fiber. In one embodiment, the six illumination fibers are arranged annularly. In one embodiment, the collection optical fiber is centrally positioned within the annular illumination fibers.

In one embodiment, the bent portion of the probe tip has a length in the range of about 0.1 mm to 10 mm. In one embodiment, the probe tip includes a reflecting prism positioned in the bend, wherein the first end of the at least one optical fiber is optically connected to a first face of the prism. In one embodiment, the probe tip includes an optically transmissive spacer optically connected to a second face of the prism. In one embodiment, the optically transmissive spacer is a cylinder with a length in the range of 0.1 mm to 10 mm.

In one embodiment, the probe tip further includes an air gap, a vacuum cavity, a gaseous gap, or at least one second optical fiber positioned between the optically transmissive spacer and optically connected to the second face of the prism.

In one embodiment, the handle includes at least one groove, and the handle includes at least one orientation projection. In one embodiment, the cable includes a bifurcation. In one embodiment, the cable comprises an optical cable including optical connectors connected to the proximal end. In one embodiment, the optical connectors comprise SubMiniature version A (SMA) connectors.

In another aspect, an arthroscopic probe system comprises a light source, a spectrometer including a photosensor, an arthroscopic probe device communicatively connected to the spectrometer, and a computing system communicatively connected to the spectrometer.

In one embodiment, the computing system comprises a non-transitory computer-readable medium with instructions stored thereon, that when executed by a processor, perform the step of calculating a composition of a measured substance or material based on spectral data.

In one embodiment, the arthroscopic probe device comprises a probe shaft including a proximal end and probe tip positioned at a distal end, a handle including a proximal end and a distal end, wherein the distal end of the handle is connected to the proximal end of the probe shaft, a cable including a first end and a second end, wherein the first end is connected to the proximal end of the handle, and at least one optical fiber, wherein a first end the at least one optical fiber is optically connected to the probe tip, wherein the at least one optical fiber is positioned internally to the probe shaft, handle and cable, and wherein a second end of the at least one optical fiber terminates at the second end of the cable.

In one embodiment, the arthroscopic probe device is communicatively connected via a bifurcated cable to the light source and the photosensor of the spectrometer. In one embodiment, the connection between the arthroscopic probe device and the spectrometer comprises an optical connection.

In another aspect, an arthroscopy method comprises providing the system as described above, placing the probe tip proximate to a substance or material to be measured, supplying light via the light source to the substance or material to be measured via the at least one optical fiber, collecting spectral data via the at least one optical fiber, measuring the spectral data via the photosensor, and calculating a composition of the substance or material based on the spectral data.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 8 is a flow chart depicting an exemplary arthroscopy method in accordance with some embodiments.

DETAILED DESCRIPTION OF THE INVENTION

Figure 1:
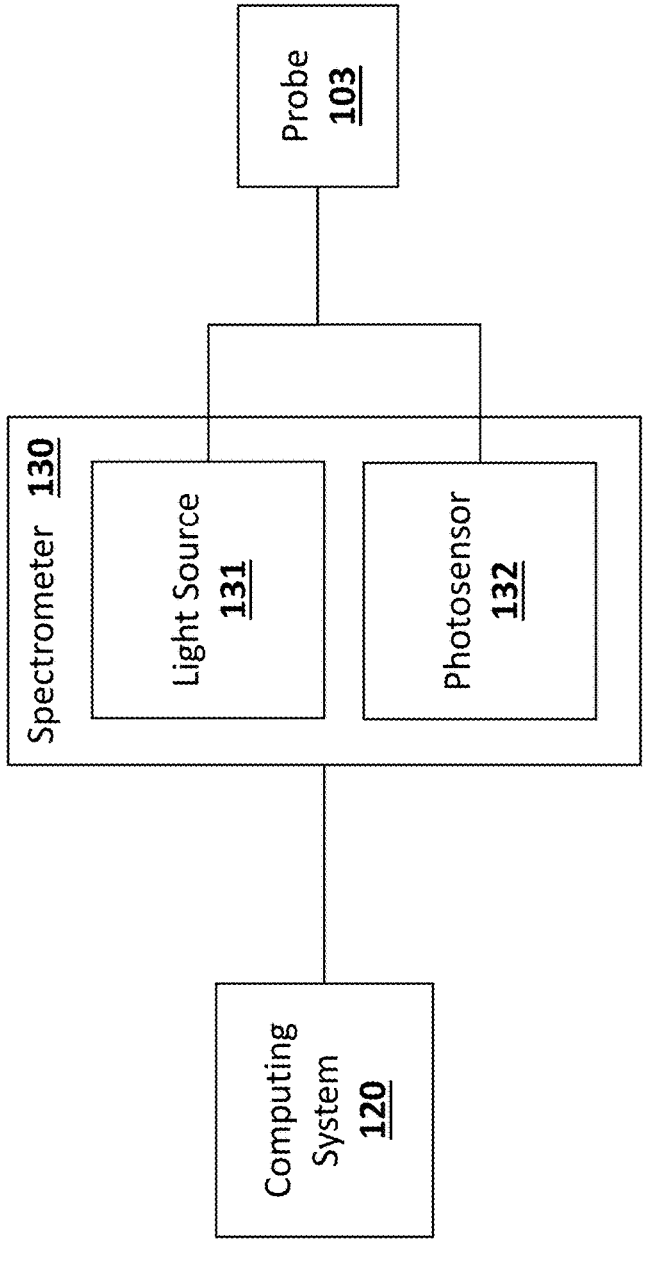
FIG. 1 is a block diagram depicting an exemplary arthroscopic probe system in accordance with some embodiments.

It is to be understood that the figures and descriptions of the present invention have been simplified to illustrate elements that are relevant for a clearer comprehension of the present invention, while eliminating, for the purpose of clarity, many other elements found in systems and methods of arthroscopic probes. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of +20%, ±10%, 5%, 1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein a VNIR arthroscopic probe device, system and method.

There are currently no commercially available fiber optic probes that span the NIR or visible NIR (VNIR) spectral range to assess cartilage quality during surgery or other clinical arthroscopic investigations. The VNIR arthroscopic probe proposed herein fills this demand and is an innovative technology that has the potential to significantly improve joint cartilage assessment and therapeutic management. Interobserver evaluation in real-time arthroscopic cartilage grading results in subjective grading that is not satisfactory, thus emphasizing the need for objective measurement techniques for arthroscopic cartilage grading.

Disclosed herein is a system device and method to provide real time analysis of joint tissues by a visible to near infrared VNIR spectral probe that allows for the objective evaluation of compositional properties during arthroscopy that are typically correlated with mechanical properties. The non-destructive VNIR probe represents a fundamentally new and powerful approach for evaluating tissue quality and guiding cartilage therapeutics. It is advantageous in comparison to the current joint assessment procedure of subjective palpation and interpretation using the traditional arthroscopic hook probe by providing objective quantitative information. The VNIR arthroscopic probe was designed with clinicians in mind to guide management of joint diseases. Furthermore, it is capable of obtaining compositional information from tissues based on spectral data.

Some aspects of the present invention may be made using an additive manufacturing (AM) process. Among the most common forms of additive manufacturing are the various techniques that fall under the umbrella of "3D Printing", including but not limited to stereolithography (SLA), digital light processing (DLP), fused deposition modelling (FDM), selective laser sintering (SLS), selective laser melting (SLM), electronic beam melting (EBM), and laminated object manufacturing (LOM). These methods variously "build" a three-dimensional physical model of a part, one layer at a time, providing significant efficiencies in rapid prototyping and small-batch manufacturing. AM also makes possible the manufacture of parts with features that conventional subtractive manufacturing techniques (for example CNC milling) are unable to create.

Suitable materials for use in AM processes include, but are not limited to, using materials including but not limited to nylon, polyethylene terephthalate (PET), acrylonitrile butadiene styrene (ABS), resin, polylactic acid (PLA), polystyrene, and the like. In some embodiments, an AM process may comprise building a three-dimensional physical model from a single material, while in other embodiments, a single AM process may be configured to build the three-dimensional physical model from more than one material at the same time.

FIG. 1 shows an exemplary arthroscopic probe system 100. In some embodiments, the system 100 includes a spectrometer 130, an arthroscopic probe device 103 communicatively connected to the spectrometer 130, and a computing system 120 communicatively connected to the spectrometer 130. In some embodiments, the spectrometer 130 includes a light source 131 and a photosensor 132. In some embodiments, the light source 131 is external to the spectrometer 130. The light source 131 can be any suitable light source including, but not limited to, an incandescent light source, a light emitting diode (LED), a laser, a fluorescent light source, xenon lamp, deuterium lamp, tungsten lamp, halogen lamps, a Globar source and any other sources that span the visible-near infrared spectral range of about 380-2500 nm (equivalent to 26,316-4000 cm$^{-1}$ in frequency units), and any combination thereof. The photosensor can be any suitable photosensor including, but not limited to, a photodiode, a photomultiplier, a CCD, a silicon photomultiplier, a phototube, a photocathode, a photoresistor, a phototransistor, a CMOS detector, and any other suitable detector or combination thereof. Specific materials for detectors may include but are not limited to thermal or quantum detectors comprised of graphene, carbon nanotubes, SiGe, InGaAs, PbS, PbSe, InAsSb, and any other suitable material or combination thereof.

In some embodiments, the connection between the arthroscopic probe device 103 and the spectrometer 130 comprises an optical connection. In some embodiments, the probe device 103 is communicatively connected via a bifurcated cable to the light source 131 and the photosensor 132 of the spectrometer 130.

In some embodiments, the computing system comprises a non-transitory computer-readable medium with instructions stored thereon, that when executed by a processor, perform the step of calculating a composition of a measured substance or material based on spectral data.

In some embodiments, the communicative connection between the computing system 120 and the spectrometer 130, as well as the communicative connection between the spectrometer 130 and the probe 103, can each independently be wired and/or wireless. Wired connections can include ethernet, optical, coaxial, fiber optic, or any other suitable wired connection or combinations thereof. Wireless connections can include Bluetooth, Near-Field Communication (NFC), infrared, Wi-Fi, and any other suitable wireless connection or combinations thereof.

Figure 2:
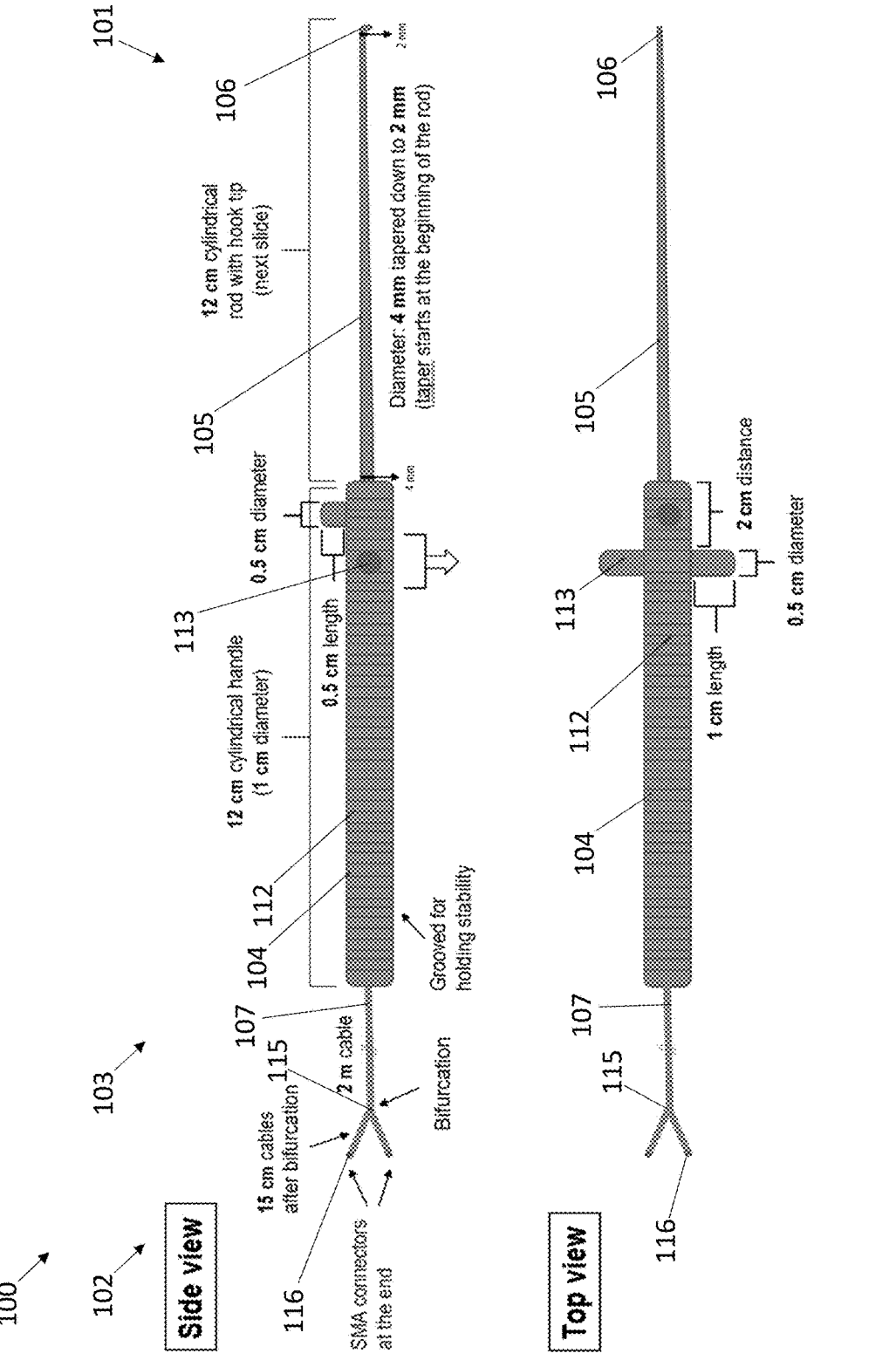
FIG. 2 depicts top and side views of an exemplary arthroscopic probe in accordance with some embodiments.
Figure 3:
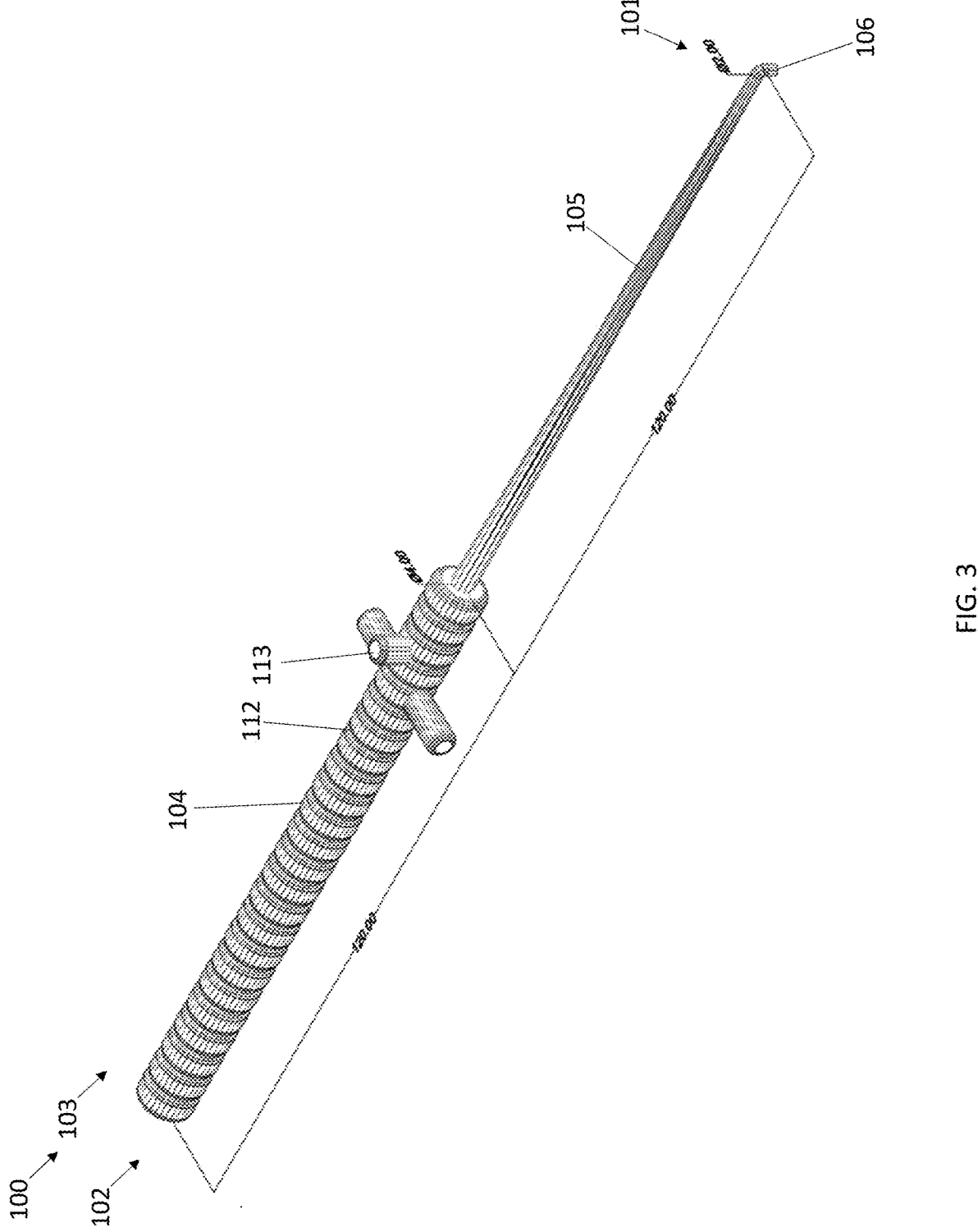
FIG. 3 depicts a perspective view of an exemplary arthroscopic probe in accordance with some embodiments.
Figure 4:
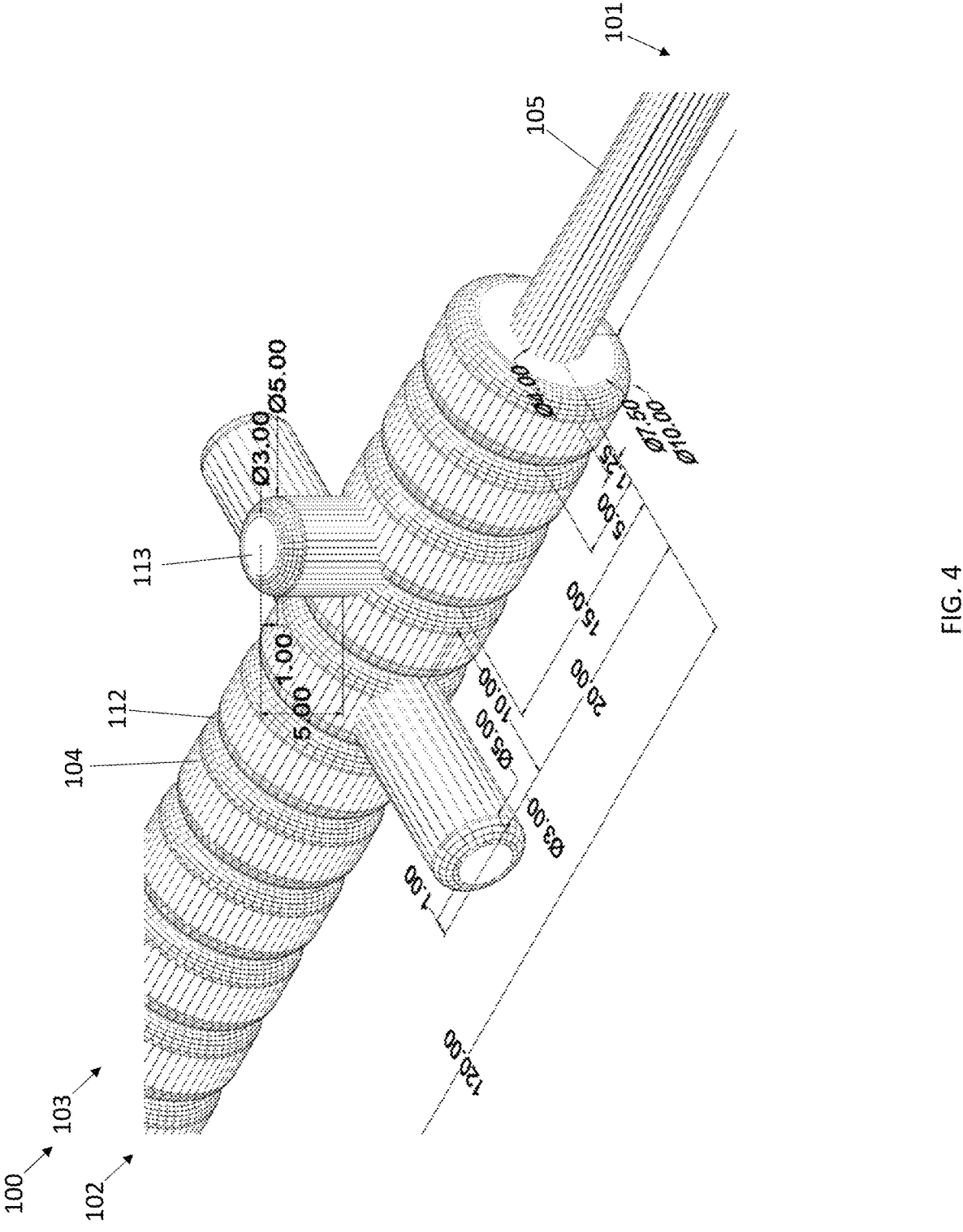
FIG. 4 depicts an enlarged perspective view of an exemplary arthroscopic probe in accordance with some embodiments.
Figure 5:
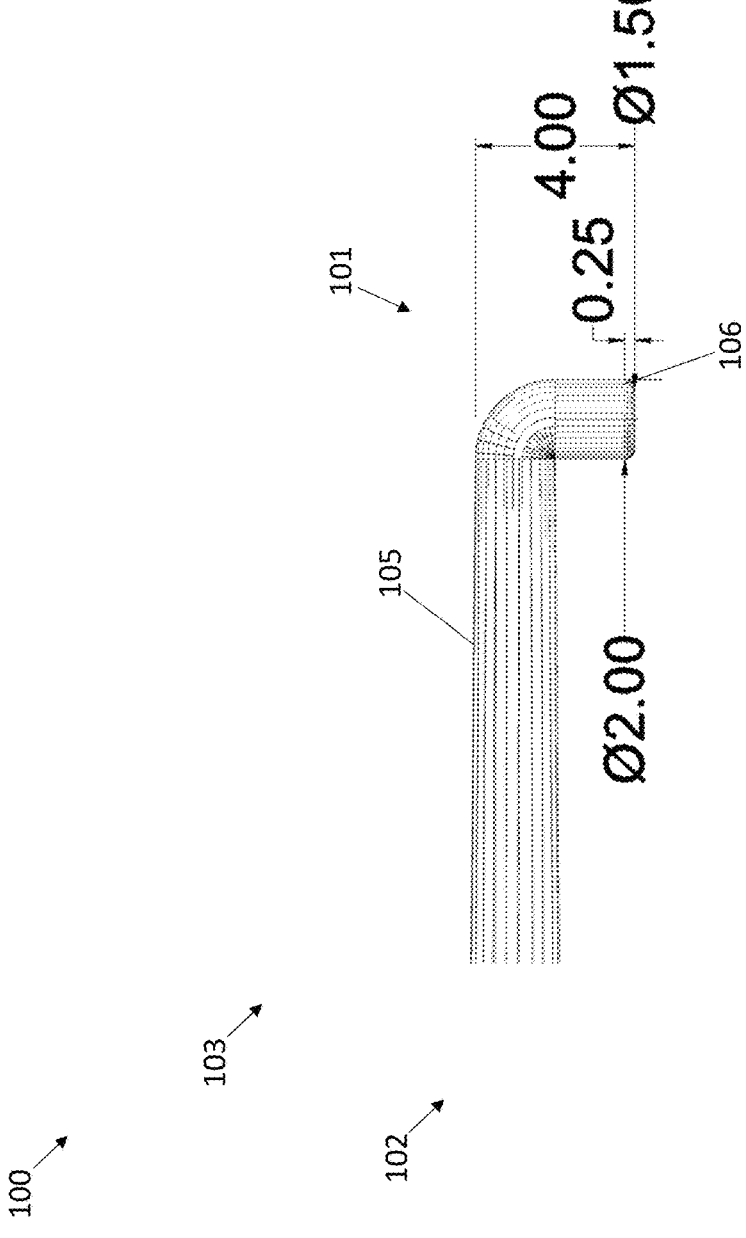
FIG. 5 depicts an enlarged side view of a distal end of an exemplary arthroscopic probe in accordance with some embodiments.
Figure 6A:
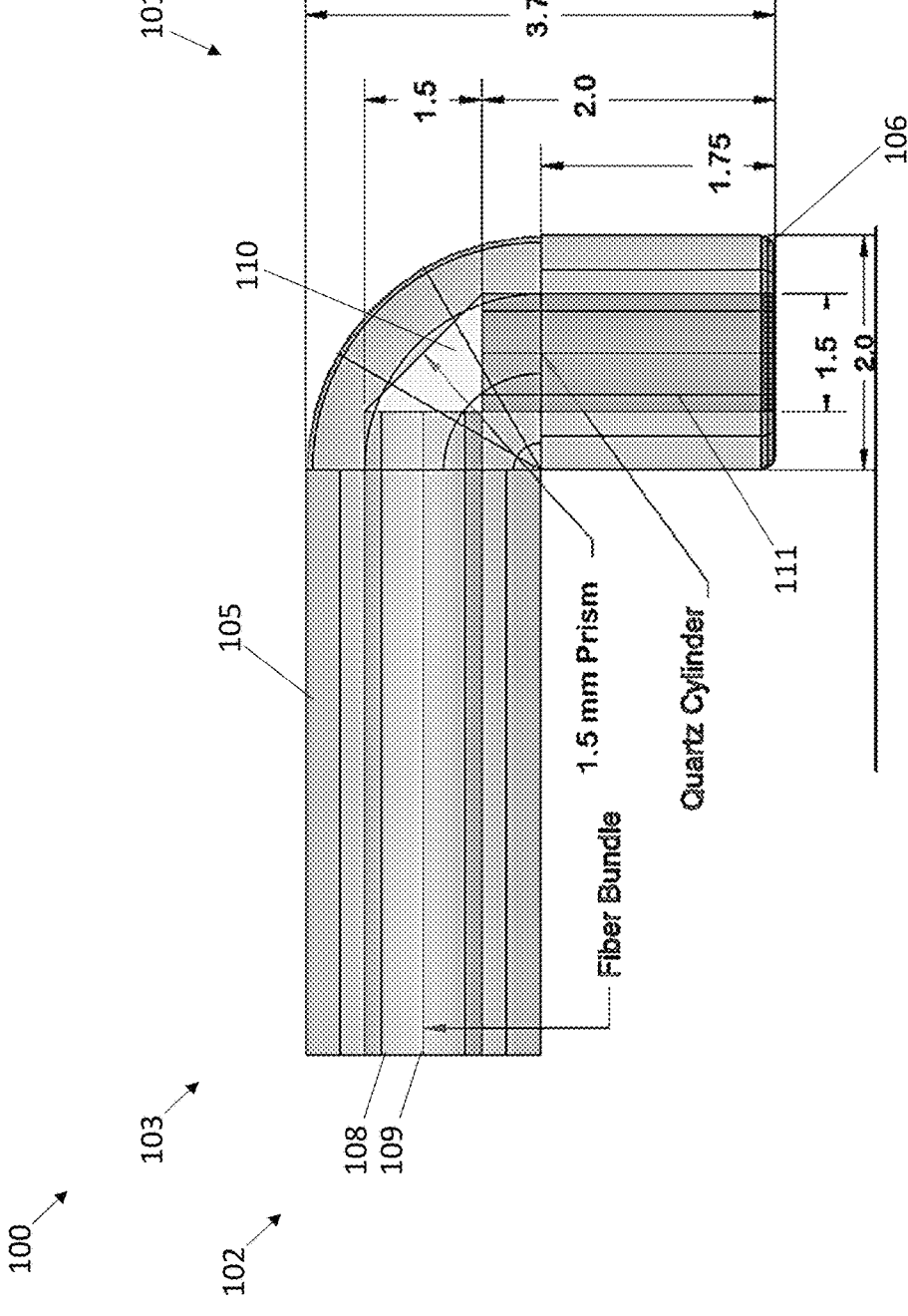
FIG. 6A depicts a cutaway side view of a distal end of an exemplary arthroscopic probe in accordance with some embodiments.
Figure 6B:
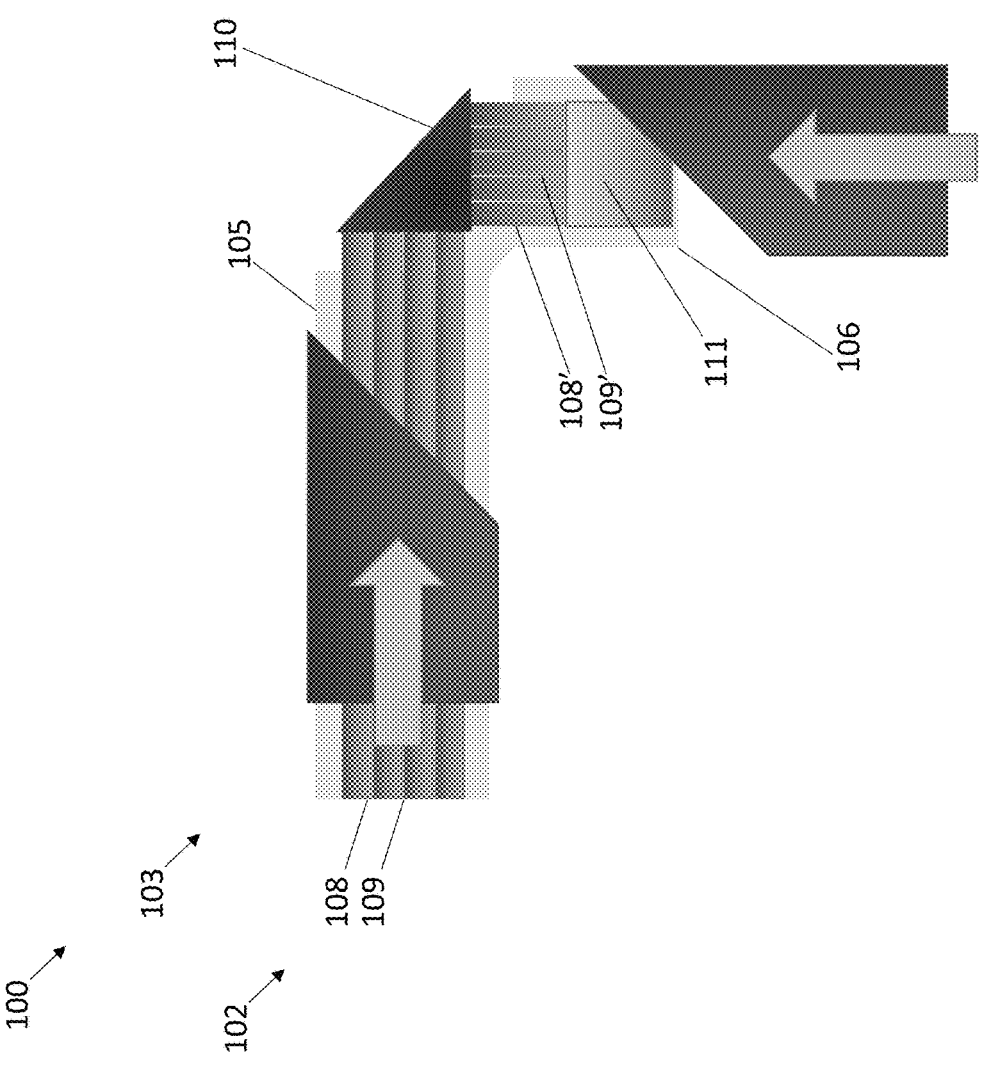
FIG. 6B depicts a cutaway side view of a distal end of another exemplary arthroscopic probe in accordance with some embodiments.
Figure 7:
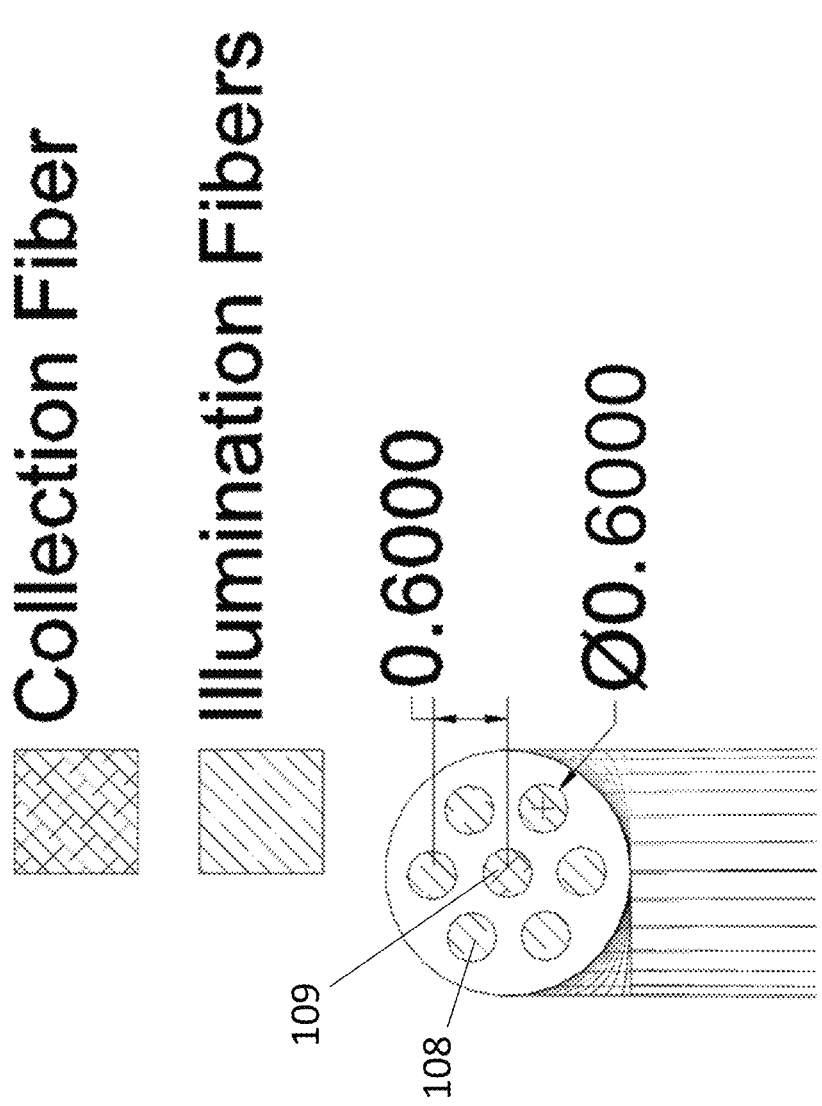
FIG. 7 depicts an enlarged distal end view of an exemplary arthroscopic probe in accordance with some embodiments.

FIGS. 2-7 show details of an exemplary VNIR arthroscopic probe 103. FIG. 2 depicts top and side views of an exemplary arthroscopic probe 103. FIG. 3 depicts a perspective view of an exemplary arthroscopic probe 103. FIG. 4 depicts an enlarged perspective view of an exemplary arthroscopic probe 103. FIG. 5 depicts an enlarged side view of a distal end of an exemplary arthroscopic probe 103. FIGS. 6A and 6B depict cutaway side views of distal ends of exemplary arthroscopic probes 103. FIG. 7 depicts an enlarged distal end view of an exemplary arthroscopic probe 103.

In some embodiments the arthroscopic probe device 103 includes a probe shaft 105 including a proximal end 102 and a probe tip 106 positioned at a distal end 101. The probe 103 further includes a handle 104 with proximal 102 and distal 101 ends. The distal end 101 of the handle 104 is connected to the proximal end 102 of the probe shaft 105. A hollow cable 107 including a first (distal) end and a second (proximal) end, where the first end is connected to the proximal end 102 of the handle 104 with glue or other appropriate materials or devices to secure the two parts, is also included.

In some embodiments the probe 103 further includes at least one optical fiber (108, 109), where a first (distal) end the at least one optical fiber (108, 109) is optically connected to or threaded through the probe tip 106, the at least one optical fiber (108, 109) is threaded or positioned internally through the probe shaft 105, handle 104 and cable 107, and where a second (proximal) end of the at least one optical fiber (108, 109) terminates at the second (proximal) end of the cable 107.

In some embodiments, the probe shaft 105 comprises a hollow cylinder. In some embodiments, the probe shaft 105 comprises a hollow cylinder with a wall thickness of about 0.05 mm to 1 mm, 0.1 mm to 0.5 mm, about 0.25 mm, or any other suitable wall thickness that enables arthroscopic investigation of articulating joints of humans and large animal models (including pigs, sheep, horses, cows). In some embodiments, the probe shaft 105 has a diameter of about 0.1 mm to 10 mm, about 1 mm to 5 mm, about 2 mm to 4 mm, about 2 mm, about 4 mm, or any other suitable diameter. In some embodiments the probe shaft 105 is tapered from the proximal end 102 to the distal end 101. The probe shaft 105 can have any suitable proximal to distal taper such as about 0.5 mm to 10 mm proximal end diameter to about 0.1 mm to 8 mm distal end diameter, or about 4 mm proximal end diameter to about 2 mm distal end diameter. In some embodiments, the probe shaft diameter and/or taper are configured to enable arthroscopic investigations of articulating joints of humans and animal models. In some embodiments, the probe shaft 105 can be manufactured via 3D printing.

In some embodiments, the probe shaft 105 has a length of about 1 cm to 25 cm, about 5 cm to 20 cm, about 10 cm to 15 cm, about 12 cm, or any other suitable length. In some embodiments, the probe shaft 105 comprises stainless steel, titanium, metal alloy, bio-compatible material, composite, polymer, resin, glass, or any other suitable material or combination thereof.

In some embodiments, the handle 104 includes at least one groove 112 or other textured pattern to facilitate gripping, and/or at least one orientation projection 113. The at least one groove 112 can be configured to provide enhanced grip and stability to prevent slipping when the probe is in use. The at least one orientation projection 113 can be configured to provide feedback as to the orientation of the probe tip 106 to a user.

In some embodiments, the handle 104 comprises a cylinder. In some embodiments, the handle 104 comprises a hollow cylinder with a wall thickness of about 1 mm to 10 mm, about 4 mm to 8 mm, about 6 mm, or any other suitable wall thickness. In some embodiments, the handle 104 has a diameter of about 0.1 cm to 10 cm, about 0.5 cm to 5 cm, about 0.5 cm to 1.5 cm, about 1 cm, or any other suitable diameter or combination thereof. In some embodiments, the handle 104 can be manufactured via 3D printing.

In some embodiments, the handle 104 has a length of about 1 cm to 25 cm, about 5 cm to 20 cm, about 10 cm to 15 cm, about 12 cm, or any other suitable length or combination thereof. In some embodiments, the handle 104 comprises stainless steel, titanium, metal alloy, bio-compatible material, composite, polymer, resin, glass, or any other suitable material or combination thereof.

In some embodiments, the at least one groove 112 has a depth of about 1 mm to 10 mm, 1 mm to 3 mm, about 2 mm, about 2.5 mm, or any other suitable depth. In some embodiments, the edges of the at least one groove are radiused. In some embodiments, the at least one groove 112 is integral to the handle 104. In some embodiments, the at least one groove 112 comprises a plurality of grooves 112 spaced apart about 0.1 cm to 1 cm, about 0.5 cm, or any other suitable spacing.

In some embodiments, the at least one orientation projection 113 has a diameter of about 0.1 cm to 5 cm, about 0.1 to 1 cm, about 0.5 cm, or any other suitable diameter, and a length of about 0.1 cm to 5 cm, about 0.1 cm to 2 cm, about 1 cm, or any other suitable length. In one embodiment, the at least one orientation projection 113 is integral to the handle 104. In some embodiments, the at least one orientation projection 113 comprises a top or bottom projection and two lateral projections. In some embodiments, the at least one orientation projection 113 comprises at least one of a circular cylinder, an elliptic cylinder, a cube, a teardrop, a semi-sphere, or any other suitable shape or combination thereof.

In some embodiments, the at least one optical fiber comprises six illumination optical fibers 108 and one collection optical fiber 109. The six illumination optical fibers 108 can be arranged annularly, linearly, squarely, rectangularly, triangularly, randomly, or any other suitable arrangement or combination thereof. In some embodiments the collection optical fiber 109 is centrally positioned within the arrangement of illumination optical fibers 108. In some embodiments, the center-to-center spacing between an optical fiber (108, 109) and its nearest neighboring optical fibers (108, 109) is about 100 μm to 2000 μm, about 500 μm to 1000 μm, about 600 μm, or any other suitable spacing.

In some embodiments, there are a plurality of illumination optical fibers 108 arranged annularly, linearly, squarely, rectangularly, triangularly, randomly, or any other suitable arrangement or combination thereof. In some embodiments, there are a plurality of collection optical fibers 109 arranged annularly, linearly, squarely, rectangularly, triangularly, randomly, or any other suitable arrangement or combination thereof among the plurality of illumination optical fibers 108.

In some embodiments, the first end of the illumination optical fibers 108 and the first end of the illumination optical fiber 109 terminate at a prism 110 positioned in the probe tip 106. In some embodiments, the second end of illumination optical fibers 108 terminate at one of the bifurcated second ends of the cable 107, and the second end of collection optical fiber 109 terminates at the other bifurcated second end of the cable 107. In some embodiments, the first end of the illumination optical fibers 108 and the first end of the illumination optical fiber 109 terminate at a point about 0.1 mm to 5 mm from the end the probe tip 106, and the fibers (108, 109) include a bend at an angle in the range of about 50 degrees to 150 degrees, about 80 degrees to 120 degrees, about 80 degrees, about 90 degrees, about 100 degrees, about 110 degrees, about 120 degrees, or any other suitable angle. In some embodiments, the first end of the illumination optical fibers 108 and the first end of the illumination optical fiber 109 terminate at the end the probe tip 106, and the fibers (108, 109) include a bend at an angle in the range of about 50 degrees to 150 degrees, about 80 degrees to 120 degrees, about 80 degrees, about 90 degrees, about 100 degrees, about 110 degrees, about 120 degrees, or any other suitable angle.

In some embodiments, the at least one optical fiber (108, 109) has a diameter of about 100 μm to 1000 μm, about 250 μm to 750 μm, about 400 μm to 600 μm, about 400 μm, about 500 μm, about 600 μm, or any other suitable diameter. In some embodiments, the at least one optical fiber (108, 109) has a length of about 5 cm to 500 cm, about 100 cm to 400 cm, about 200 cm to 300 cm, about 240 cm, about 250 cm, or any other suitable length. In some embodiments, the at least one optical fiber (108, 109) comprises low-OH quartz, visible to near infrared (Vis-NIR) quartz, fused silica, borosilicate, silver halide, chalcogenide, or any other suitable material or combination thereof. Fiber optic cladding may also be used to prevent fiber signal crosstalk.

In some embodiments, the cable 107 comprises an optical cable including optical connectors connected to the proximal end. In some embodiments, the cable 107 includes a bifurcation 115 splitting the second end into two ends. In some embodiments, the optical connectors comprise SubMiniature version A (SMA) connectors, FC/PC connectors, FC/APC connectors, ST/PC connectors and any other suitable connector or combination thereof.

In some embodiments, the cable 107 has a length of about 10 cm to 500 cm, about 100 cm to 300 cm, about 200 cm, about 215 cm, or any other suitable length. In some embodiments, the bifurcated portions of the cable 107 each have a length of about 1 cm to 50 cm, about 10 cm to 20 cm, about 15 cm, or any other suitable length.

Referring now to FIGS. 5-7, exemplary details of the probe tip 106 are shown. In some embodiments, the probe tip includes a bend in relation to a central longitudinal axis of the probe shaft 105 at an angle in the range of about 50 degrees to 150 degrees, about 80 degrees to 120 degrees, about 80 degrees, about 90 degrees, about 100 degrees, about 110 degrees, about 120 degrees, or any other suitable angle. In some embodiments, the length of the bent portion from the distal most tip to a central longitudinal axis of the probe shaft 105 is about 0.1 mm to 10 mm, about 1 mm to 7 mm, about 3 mm to 5 mm, about 4 mm, less than 5 mm, less than 4 mm, or any other suitable length. In some embodiments, the edges of the tip 106 are molded with a fillet radius.

In some embodiments, the probe tip 106 includes a reflecting prism 110 positioned in the bend, where the first end of the at least one optical fiber (108, 109) is optically connected to a first face of the prism 110. The probe tip 106 can further include an optically transmissive spacer 111. In some embodiments the optically transmissive spacer 111 is optically connected to a second face of the prism 110 and positioned between the prism 110 and a contact point at the distal most end of the tip 106. In some embodiments, the spacer 111 comprises a cylinder, a hollow cylinder, a cylinder including channels, or other suitable shape. In some embodiments, the spacer 111 has a length of about 0.1 mm to 10 mm, about 1 mm to 5 mm, about 2 mm, or any other suitable length. In some embodiments, the space 111 has a diameter of about 0.1 mm to 10 mm, about 1 mm to 5 mm, about 1.5 mm, or any other suitable diameter. In some embodiments, the spacer 111 comprises VNIR transmissive glass, quartz, fuse silica, borosilicate, silver halide, plastic, or any other suitable material.

In some embodiments, an air gap is positioned between the optically transmissive spacer 111 and the second face of the prism 110. In some embodiments, a vacuum cavity is positioned between the optically transmissive spacer 111 and the second face of the prism 110. In some embodiments, a gaseous gap is positioned between the optically transmissive spacer 111 and the second face of the prism 110, where the gaseous gap can include a gas comprising air, a noble gas, helium, nitrogen, argon, or any other suitable gas or combination thereof.

In some embodiments, at least one second optical fiber (108', 109') is positioned between the optically transmissive spacer 111 and the second face of the prism 110. In some embodiments, at least one second optical fiber (108', 109') is positioned between the probe tip 106 and the second face of the prism 110. In some embodiments, the at least one second optical fiber (108', 109') can have similar arrangement to the at least one optical fiber (108, 109) positioned in the probe shaft 105. In some embodiments, the light path is aligned pre-prism to post-prism.

In some embodiments, the optically transmissive spacer 111 is flush with the most distal portion of the probe tip 106. By having the spacer 111 flush with the tip, measurement of a substance or material can be directly performed without signal degradation due to influence of surrounding environmental conditions such as an environmental fluid with signals in the VNIR spectra. In some embodiments, the optically transmissive spacer 111 is recessed within the most distal portion of the probe tip 106.

FIG. 8 is a flowchart depicting an exemplary arthroscopy method 200. The method 200 starts at Operation 205, where an arthroscopic system 100 including an arthroscopic probe 103 as described herein is provided.

At Operation 210 the probe tip 106 is place proximate to a substance or material to be measured. In some embodiments, the substance or material to be measured is a joint tissue such as cartilage, meniscus, ligament, tendon, fat, bone, blood, or any other suitable tissue.

At Operation 215 light is supplied to the substance or material to be measured via the light source 131, the optical cable 107, and the at least one optical fiber (108, 109). In some embodiments the at least one optical fiber comprises a plurality of illumination optical fibers 108.

At Operation 220 spectral data is collected via the at least one optical fiber (108, 109), and transmitted via the optical fibers (108, 109) to the spectrometer 130. In some embodiments, the at least one optical fiber comprises a collection optical fiber 109.

At Operation 225 the spectral data is measured via the photosensor 132. The method 200 ends at Operation 230, where a composition of the substance or material based on the spectral data is calculated via the computing system 120.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, MATLAB, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Figure 9:
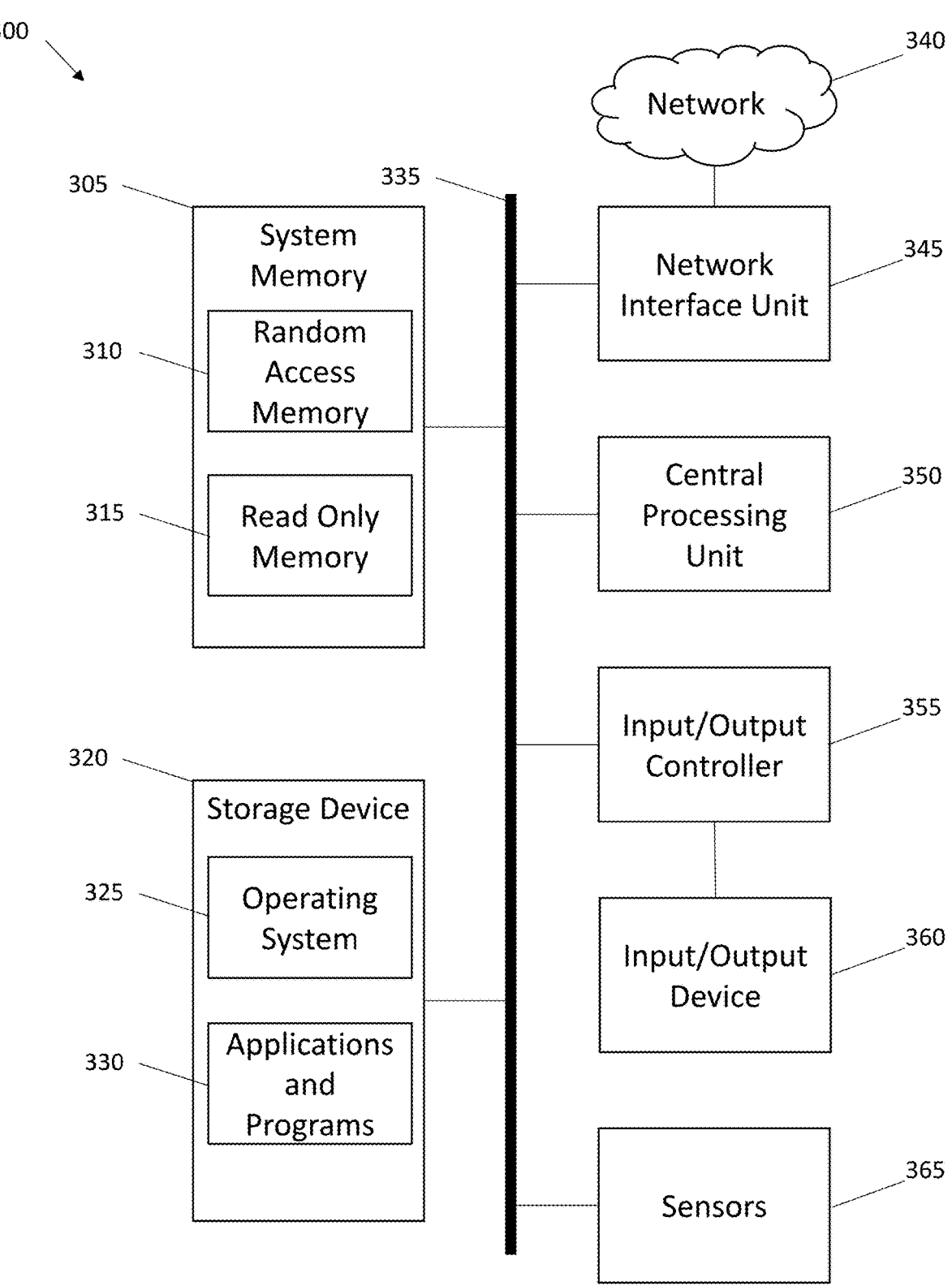
FIG. 9 is a block diagram depicting an exemplary computing system utilized by the spectroscopic arthroscopic probe system in accordance with some embodiments.

FIG. 9 and the following discussion are intended to provide a brief, general description of a suitable computing environment in which the invention may be implemented. While the invention is described above in the general context of program modules that execute in conjunction with an application program that runs on an operating system on a computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

FIG. 9 depicts an illustrative computer architecture for a computer 300 for practicing the various embodiments of the invention. The computer architecture shown in FIG. 9 illustrates a conventional personal computer, including a central processing unit 350 ("CPU"), a system memory 305, including a random-access memory 310 ("RAM") and a read-only memory ("ROM") 315, and a system bus 335 that couples the system memory 305 to the CPU 350. A basic input/output system containing the basic routines that help to transfer information between elements within the computer, such as during startup, is stored in the ROM 315. The computer 300 further includes a storage device 320 for storing an operating system 325, application/program 330, and data.

The storage device 320 is connected to the CPU 350 through a storage controller (not shown) connected to the bus 335. The storage device 320 and its associated computer-readable media, provide non-volatile storage for the computer 300. Although the description of computer-readable media contained herein refers to a storage device, such as a hard disk or CD-ROM drive, it should be appreciated by those skilled in the art that computer-readable media can be any available media that can be accessed by the computer 300.

By way of example, and not to be limiting, computer-readable media may comprise computer storage media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

According to various embodiments of the invention, the computer 300 may operate in a networked environment using logical connections to remote computers through a network 340, such as TCP/IP network such as the Internet or an intranet. The computer 300 may connect to the network 340 through a network interface unit 345 connected to the bus 335. It should be appreciated that the network interface unit 345 may also be utilized to connect to other types of networks and remote computer systems.

The computer 300 may also include an input/output controller 355 for receiving and processing input from a number of input/output devices 360, including a keyboard, a mouse, a touchscreen, a camera, a microphone, a controller, a joystick, or other type of input device. Similarly, the input/output controller 355 may provide output to a display screen, a printer, a speaker, or other type of output device. The computer 300 can connect to the input/output device 360 via a wired connection including, but not limited to, fiber optic, ethernet, or copper wire or wireless means including, but not limited to, Bluetooth, Near-Field Communication (NFC), infrared, or other suitable wired or wireless connections.

As mentioned briefly above, a number of program modules and data files may be stored in the storage device 320 and RAM 310 of the computer 300, including an operating system 325 suitable for controlling the operation of a networked computer. The storage device 320 and RAM 310 may also store one or more applications/programs 330. In particular, the storage device 320 and RAM 310 may store an application/program 330 for providing a variety of functionalities to a user. For instance, the application/program 330 may comprise many types of programs such as a word processing application, a spreadsheet application, a desktop publishing application, a database application, a gaming application, internet browsing application, electronic mail application, messaging application, and the like. According to an embodiment of the present invention, the application/program 330 comprises a multiple functionality software application for providing word processing functionality, slide presentation functionality, spreadsheet functionality, database functionality and the like.

The computer 300 in some embodiments can include a variety of sensors 365 for monitoring the environment surrounding and the environment internal to the computer 300. These sensors 365 can include a Global Positioning System (GPS) sensor, a photosensitive sensor, a gyroscope, a magnetometer, thermometer, a proximity sensor, an accelerometer, a microphone, biometric sensor, barometer, humidity sensor, radiation sensor, or any other suitable sensor.

Figure 10:
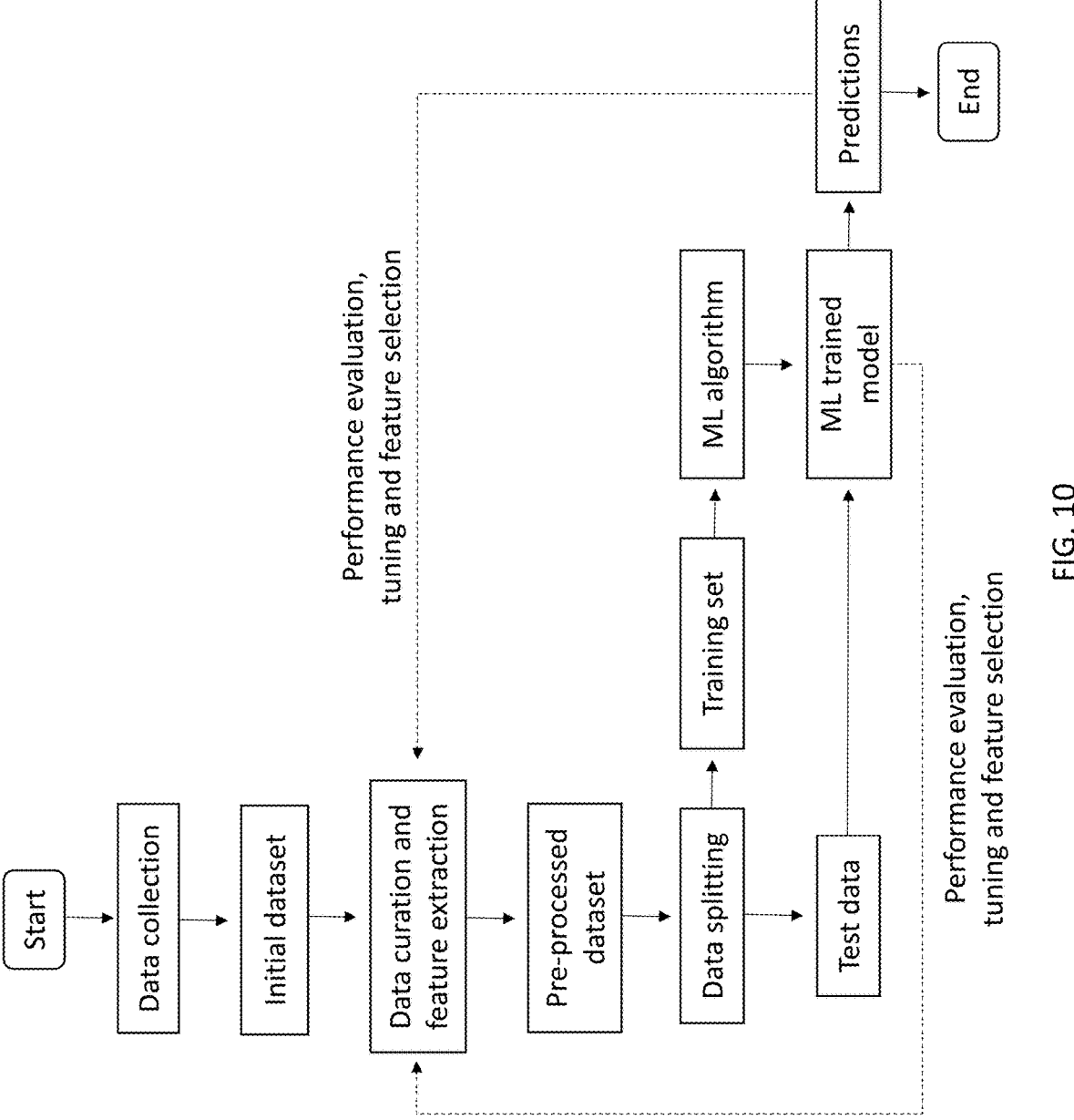
FIG. 10 depicts an illustrative flow-chart of the machine learning steps for data analysis and prediction of tissue quality outcomes based on visible-near infrared (VNIR) data in accordance with some embodiments.

In some embodiments, data analysis can include univariate or multivariate analysis, machine learning and/or AI algorithms, including but not limited to partial least squares regression, support vector machine analysis, and neural network analysis. FIG. 10 depicts an illustrative flow-chart of the machine learning steps, in which the VNIR data are the input and standard metrics of tissue quality are the predicted outcomes.

The aforementioned systems, processes and methods described herein may be utilized for desired applications as would be appreciated by those skilled in the art. For example, the system can be utilized by surgeons during routine arthroscopy to monitor joint lesions, joint lesions post-surgery, implant integration with surrounding tissue, identify optimal donor tissue sites, and identify optimal sites for autologous chondrocyte implantation. The system can furthermore provide real-time monitoring of biochemical and mechanical composition of joint and/or implant and surrounding tissue and real-time monitoring of degeneration of joint and/or implants.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out exemplary embodiments of the present invention, and are not to be construed as limiting in any way the remainder of the disclosure.

Figure 11:
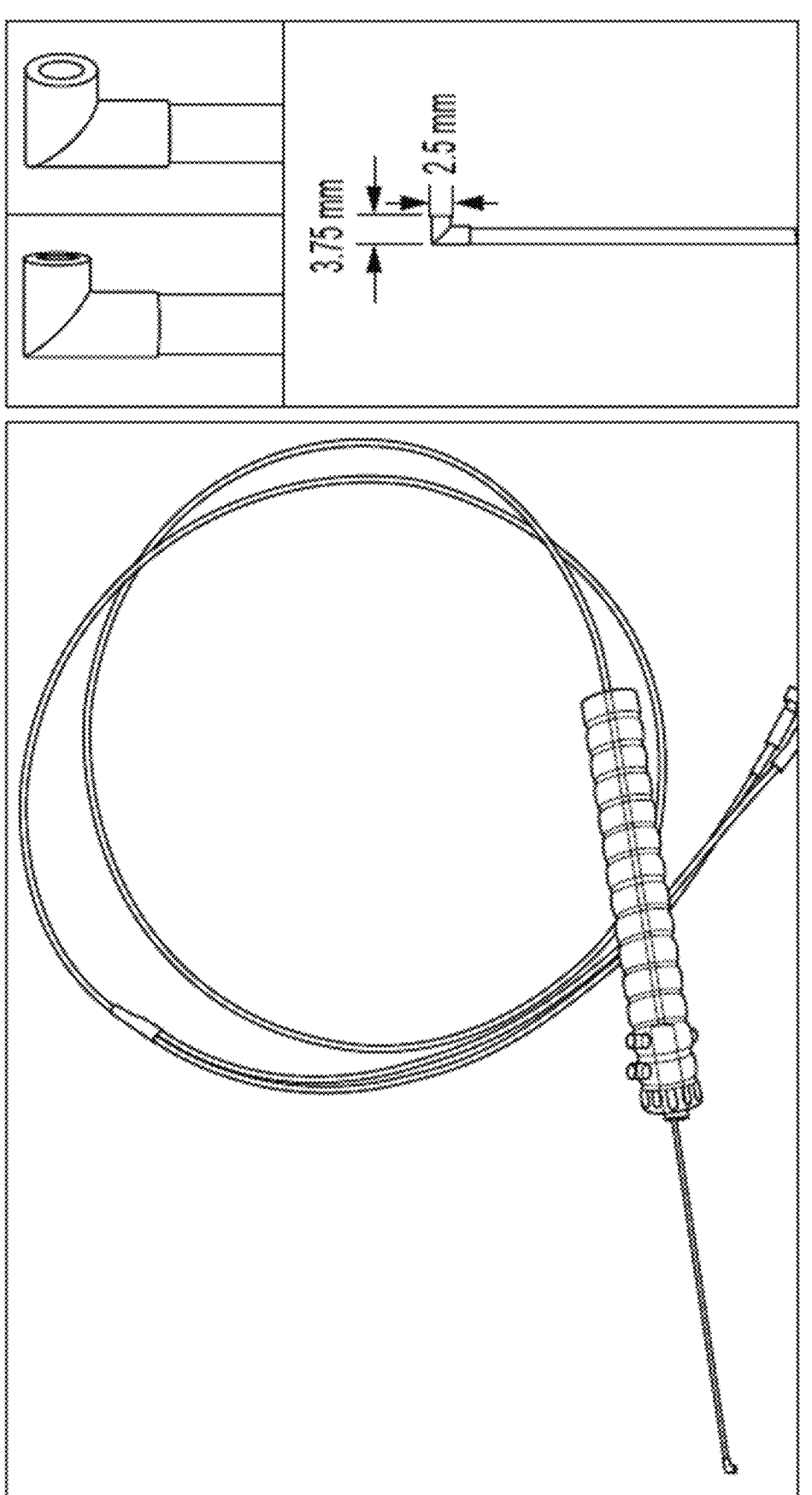
FIG. 11 depicts an experimental prototype of the arthroscopic probe device in accordance with some embodiments.

FIG. 11 shows an experimental prototype of the arthroscopic probe device 103 used for testing the system 100.

Figure 12:
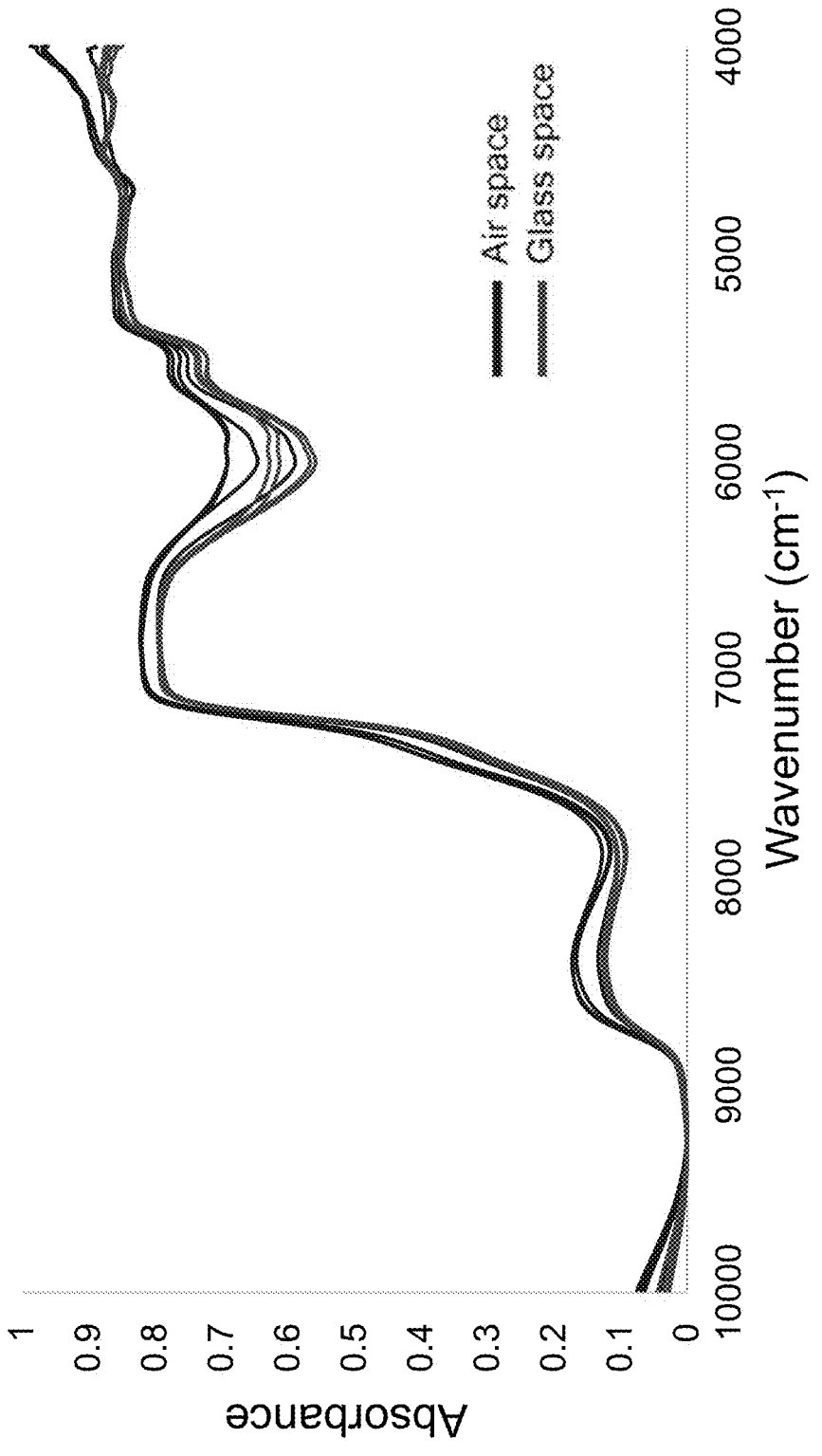
FIG. 12 is a plot showing exemplary experimental results comparing cartilage spectra collected with a 2 mm air distance vs. a 2 mm glass spacer (Pyrex) between probe and sample in accordance with some embodiments.
Figure 13:
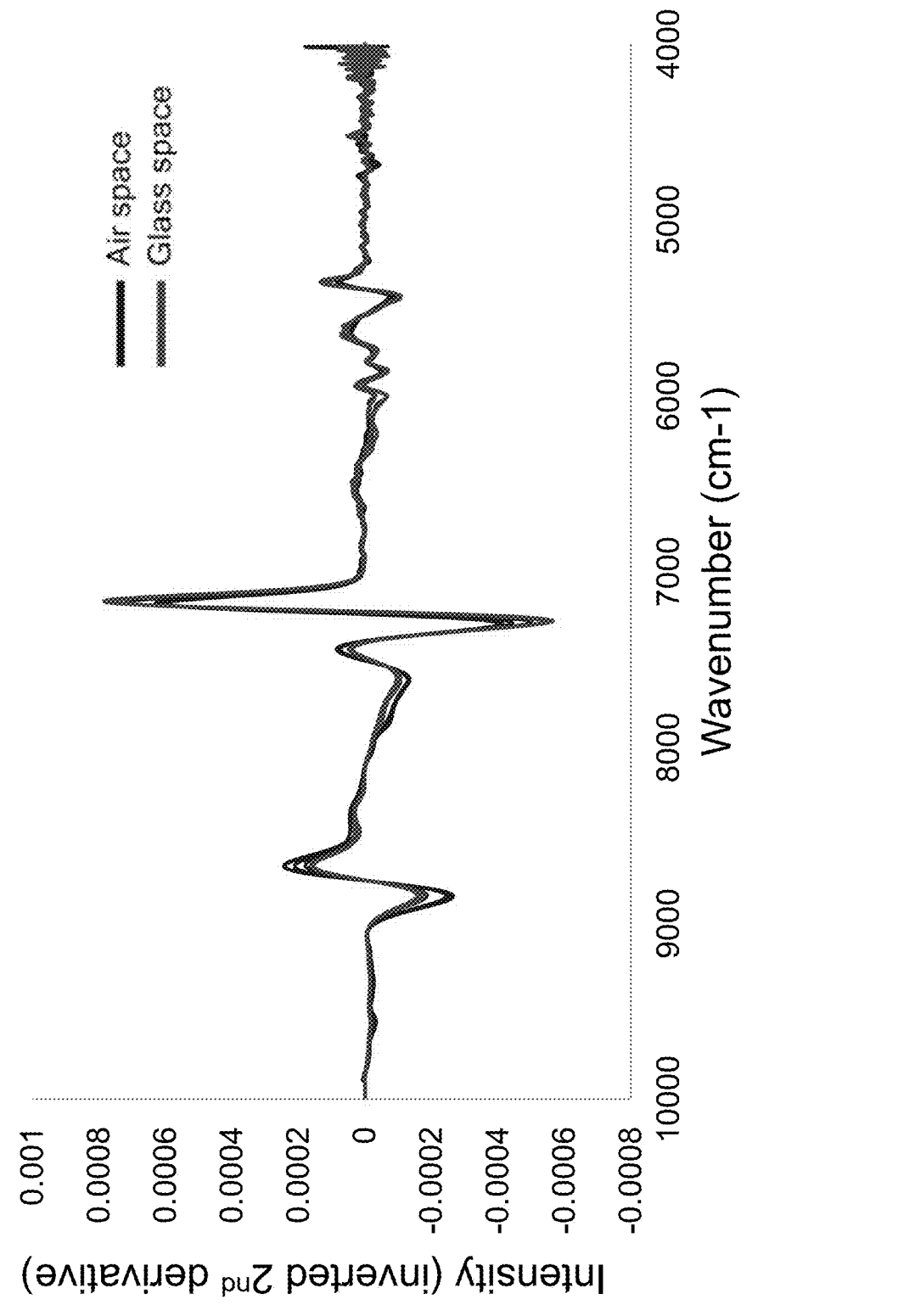
FIG. 13 is a plot showing exemplary experimental results comparing the second derivative (inverted) of the cartilage spectra in accordance with some embodiments.
Figure 14:
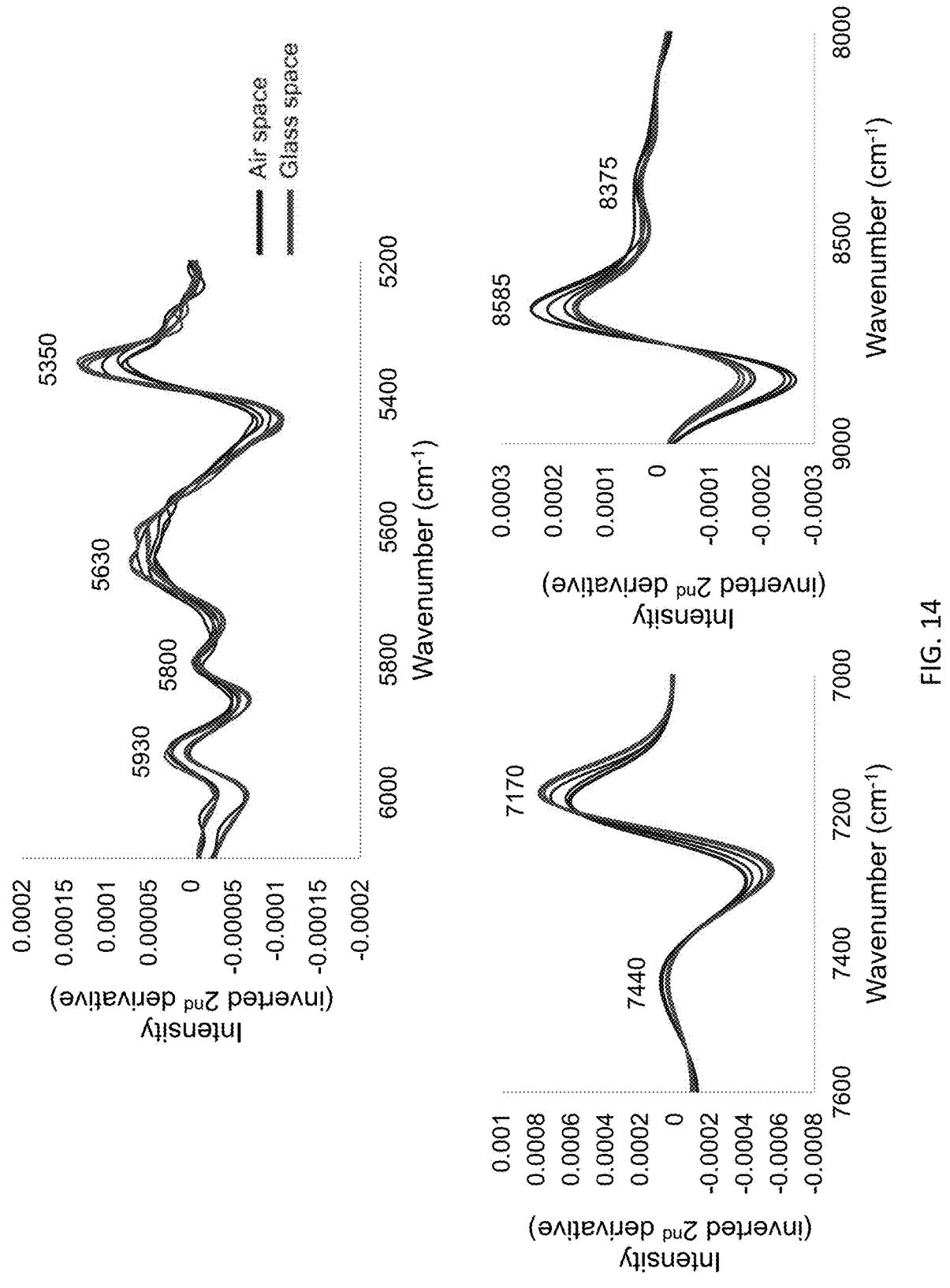
FIG. 14 are plots showing further exemplary experimental results comparing the second derivative (inverted) of the cartilage spectra in accordance with some embodiments.
Figure 15:
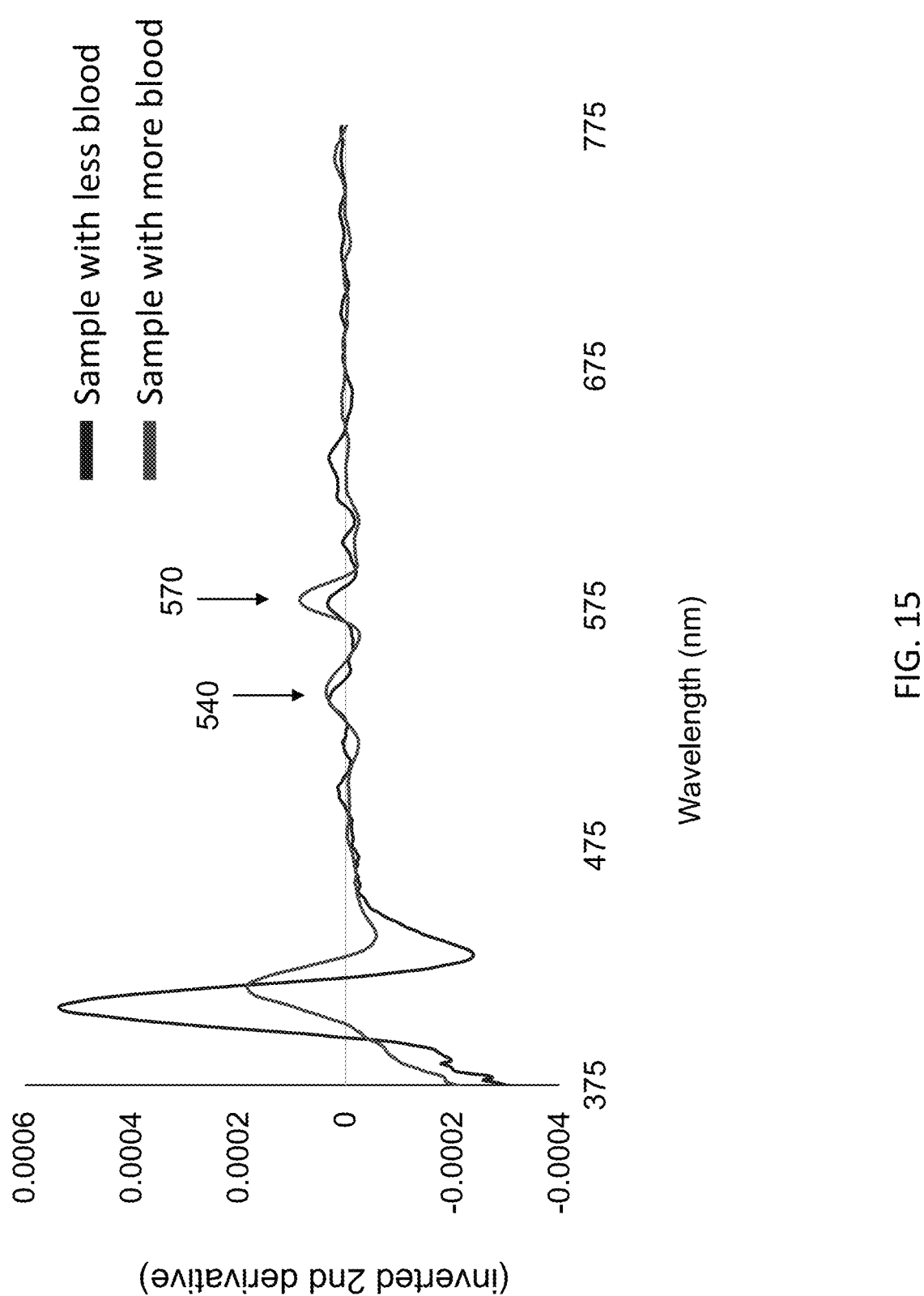
FIG. 15 is a plot showing exemplary experimental results comparing the second derivative (inverted) spectra for cartilage exemplary sample types.
Figures 16A, 16B:
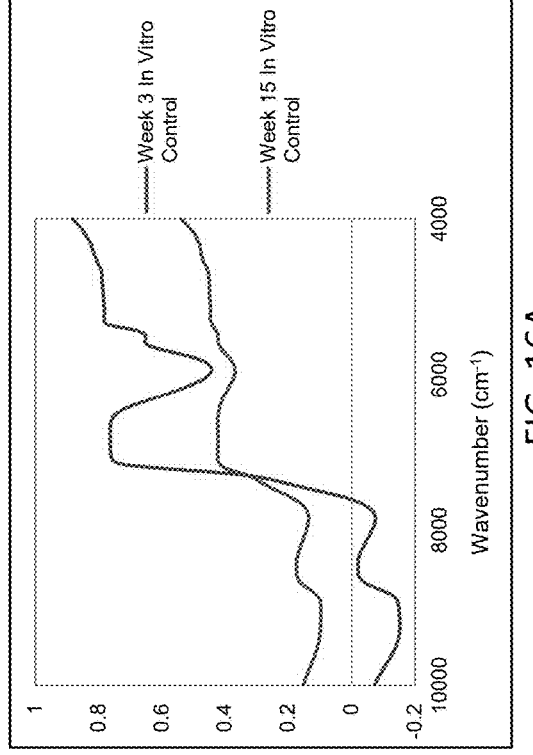
FIG. 16A through FIG. 16B show an example application of VNIR fiber optic spectroscopy used to distinguish tissue engineered cartilage at different stages of development, depicting an increase in the baseline offset of the NIR spectra (reflecting matrix formation) from 3 to 5 weeks of in vitro development in accordance with some embodiments.
Figure 17A:
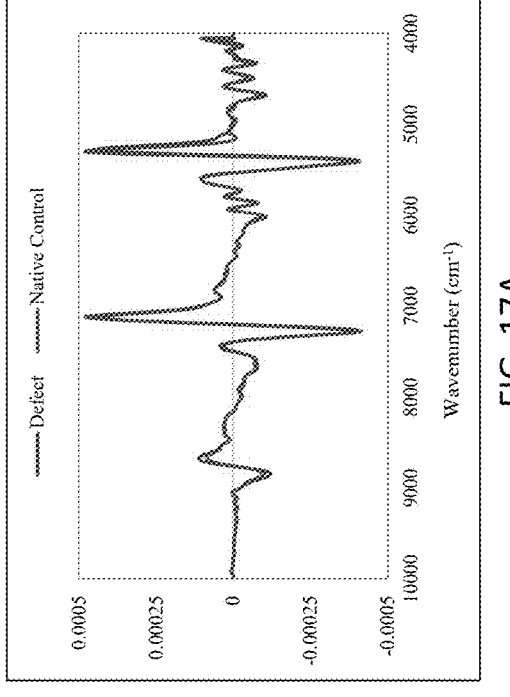
FIG. 17A through FIG. 17B show an example application of VNIR fiber optic spectroscopy to distinguish native (healthy) knee cartilage and immature repair cartilage tissue (defect), depicting a lower water peak ratio (reflecting tissue water content) in native tissue compared to the defect in accordance with some embodiments.
Figure 17B:
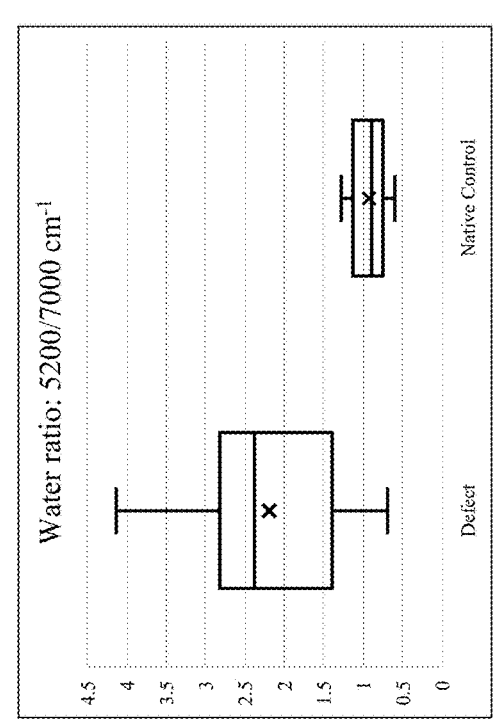
Figure 18:
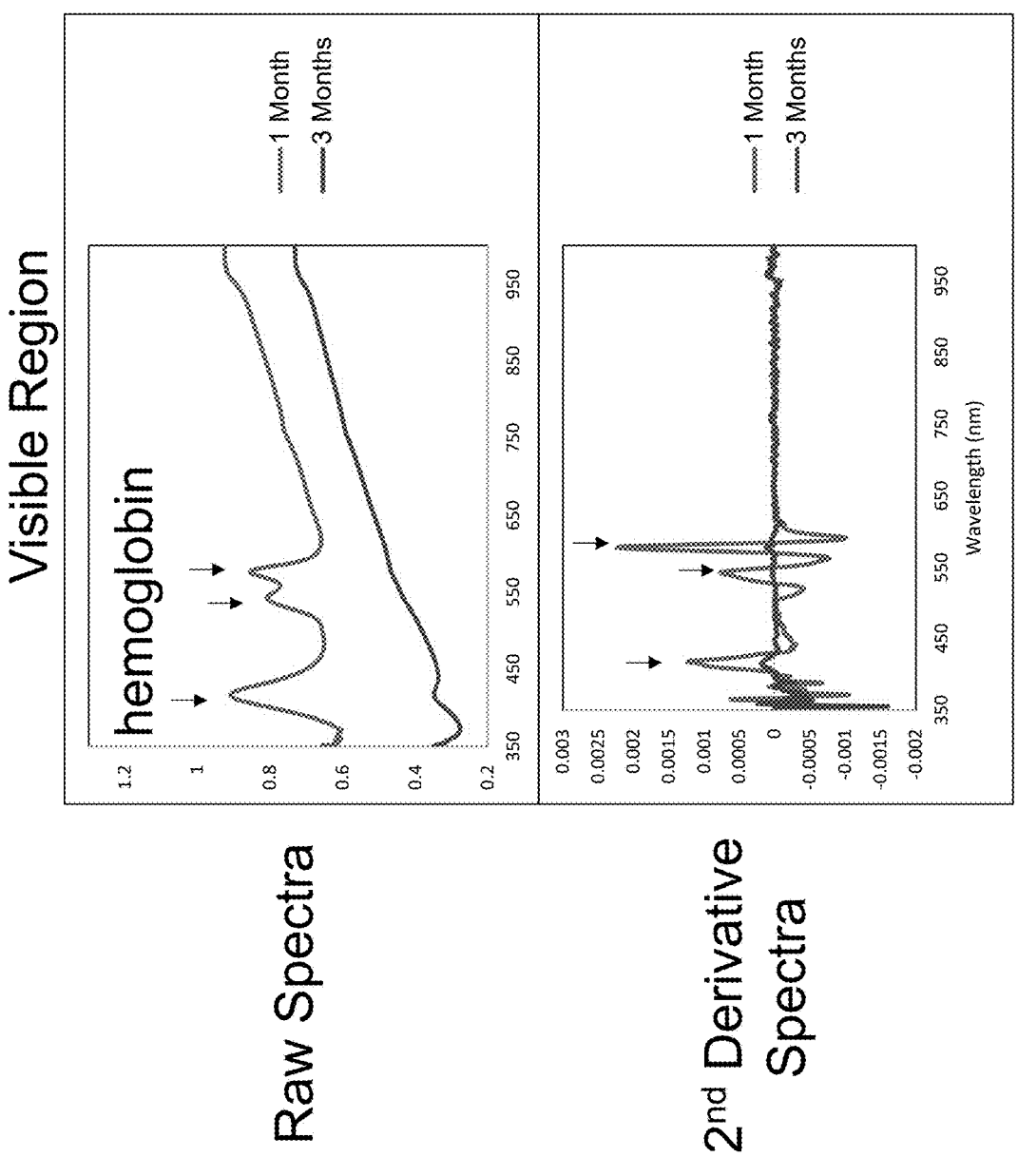
FIG. 18 shows the visible region of the VNIR spectra, which depicts a decrease in hemoglobin peaks (reflecting blood content) in cartilage repair tissue from 1 to 3 months of healing in accordance with some embodiments.

FIGS. 12-15 are plots showing example experimental results. FIG. 12 is a plot showing exemplary experimental results comparing cartilage spectra collected with a 2 mm air distance vs. a 2 mm glass spacer (Pyrex) between probe and sample. FIG. 13 is a plot showing exemplary experimental results comparing the second derivative (inverted) of the spectra. FIG. 14 are plots showing further exemplary experimental results comparing the second derivative (inverted) of the spectra. FIG. 15 shows experimental results obtained from tissues with hemoglobin (blood) absorbances detected in the visible region of the spectra. FIG. 16A through FIG. 16B show an example application of VNIR fiber optic spectroscopy used to distinguish tissue engineered cartilage at different stages of development, depicting an increase in the baseline offset of the NIR spectra (reflecting matrix formation) from 3 to 5 weeks of in vitro development. FIG. 17A through FIG. 17B show an example application of VNIR fiber optic spectroscopy to distinguish native (healthy) knee cartilage and immature repair cartilage tissue (defect), depicting a lower water peak ratio (reflecting tissue water content) in native tissue compared to the defect. FIG. 18 shows the visible region of the VNIR spectra, which depicts a decrease in hemoglobin peaks (reflecting blood content) in cartilage repair tissue from 1 to 3 months of healing. The figures further illustrate that spectral parameters of the VNIR spectra can be used to distinguish cartilage tissues with different compositional properties.

During testing it was observed that about a 1 mm to 2 mm distance between the sample surface and the fiber optics in the probe was necessary for optimal data collection. During in vitro experiments, about a 1 mm to 2 mm air distance between probe tip and samples can be easily achieved. However, during arthroscopy, the knee joint is filled with saline solution to preserve the tissue viability, which hinders regular data collection. Considering that water has major signals in the NIR spectra, it was necessary to design an approach that allows keeping about a 1 mm to 2 mm distance between the fiber optics and the samples while at the same time avoiding the influence of the surrounding water.

For this reason, the probe was equipped with a 2 mm glass spacer between the fibers in the shaft and the contact point of the tip. Furthermore, this spacer can be encased in metal, to improve the focus of the analysis on the tissue underneath the tip probe. The experimental tests showed that the data obtained with 2 mm glass spacer is comparable to that obtained with 2 mm air distance. The advantage of this innovative design by using a material that is VNIR transmissive as a spacer allows the surgeon to touch the joint cartilage with the tip of the probe while still keeping an optimal 2 mm distance between the tissue and the fiber optics. This design will improve both the practical use of the probe by surgeons and the quality of the data.

The probe quality and data collection efficacy were also tested by utilizing the probe to first measure cadaveric porcine joint tissue, and then by collect data during live porcine knee arthroscopy. Native cartilage plugs were obtained from bovine and porcine knees with a 4 mm biopsy punch. Engineered cartilage was obtained by growing porcine chondrocytes in methacrylated hyaluronic acid (meHA) gels for up to 8 weeks. The samples were analyzed with the VNIR arthroscopic probe and the raw and second derivative NIR spectra were analyzed and compared to those obtained using a standard manufactured NIR probe with similar fiber configuration to evaluate the quality and reliability of the new device with respect to assessment of properties of native and engineered cartilage.

Legs of Yucatan minipigs were obtained as surgical discards from IACUC-approved studies. The cadaveric knees were harvested and the VNIR arthroscopic probe was used to collect spectra from the joint cartilage to optimize its efficacy in a regular arthroscopy setting. From this test, the parameters were established for spectral collection (resolution, number of co-added scans, best background, and time for each spectral acquisition).

Analysis of pig knees during arthroscopy in a surgical setting was then performed. Current animal arthroscopy surgeries are held to the same standards as human surgeries. Operating rooms are fully sterile, and the surgery is performed by a trained clinician. Animal trials can serve as proxy measures for human clinical outcomes.

The effect of sterilization procedures on probe quality and performance was also evaluated. After initial testing, the probe was subjected to standard procedures for sterilization of surgical instruments and tested again using the same samples and conditions. The quality of the raw and second derivative spectra was analyzed and compared to evaluate possible changes caused by sterilization. In particular, STERRAD was initially used for sterilization. STERRAD systems use low-temperature, hydrogen peroxide gas plasma technology to sterilize a wide range of instruments efficiently, effectively and safely, for users, patients & the environment. This systems' low-temperature process provides gentle sterilization even for the most delicate instruments thereby potentially leading to longer instrument life and reduced cost of instrument repairs. At the completion of the sterilization process based on this technology, no toxic residues were observed to remain on the sterilized items. The technology is particularly suited to the sterilization of heat and moisture sensitive instruments since process temperatures do not exceed about 50 degrees C. (140 degrees F.) and sterilization occurs in a low moisture environment. The total process time is about one hour.

The efficacy of the process has been demonstrated against a broad spectrum or microorganisms and on a large number of substrates used in medical instruments. The results of the sterilization measure determine the number of surgeries than one probe can perform. Other sterilization methods, such as autoclave or ethylene oxide, are also possible.

In summary, a probe system and device for collecting visible (Vis) and NIR spectral data that reflects composition during arthroscopic procedures is disclosed. The potential of VNIR to quantify cartilage composition and mechanical properties was explored. In doing so, the disclosed embodiments fulfill the needs criteria of a non-destructive device that monitors cartilage degeneration, development and repair. Moreover, VNIR data has been shown to distinguish between ICRS score for the lesion and healthy cartilage in pre-clinical studies. Near-infrared spectroscopic analysis resulted in a good interobserver correlation and was determined a dependable method for improving the assessment of significant cartilage lesions. The data shows that changes in the composition and structure of articular cartilage influence the optical properties and can be measured objectively by VNIR spectra.

The advantages of the disclosed device and system over existing include improved arthroscopic quantitative and clinical analysis of cartilage and joint health in real-time without any specific sample preparation. This is accomplished via improved ease of use based on optimization in collection of the signal with a contact at the articular cartilage or repair tissue surface by incorporation of the space, and a bend of about 90 degrees in the probe tip.

The ease of use during arthroscopy, the quick response and the non-destructive nature of VNIR makes it a promising addition to the assessment of joint cartilage health, including cartilage, subchondral bone, meniscus, tendons, ligaments, fat, and synovium.

The following references are each hereby incorporated herein by reference in their entirety:

Yousefi, Farzad, et al. "Near-infrared spectroscopy predicts compositional and mechanical properties of hyaluronic acid-based engineered cartilage constructs." Tissue Engineering Part A 24.1-2 (2018): 106-116.

McGoverin, Cushla M., et al. "Nondestructive assessment of engineered cartilage composition by near infrared spectroscopy." Annals of biomedical engineering 44.3 (2016): 680-692.

Bonasia, Davide Edoardo, et al. "Intra- and inter-observer reliability of ten major histological scoring systems used for the evaluation of in vivo cartilage repair." Knee Surgery, Sports Traumatology, Arthroscopy 23.9 (2015): 2484-2493.

Jungmann, Pia M., et al. "Magnetic resonance imaging score and classification system (AMADEUS) for assessment of preoperative cartilage defect severity." Cartilage 8.3 (2017): 272-282.

Roos, Ewa M., et al. "ICRS recommendation document: patient-reported outcome instruments for use in patients with articular cartilage defects." Cartilage 2.2 (2011): 122-136.

Querido, William, et al. "Vibrational spectroscopy and imaging: applications for tissue engineering." Analyst 142.21 (2017): 4005-4017.

Spahn G, Plettenberg H, Kahl E, Klinger H M, Muckley T, Hofmann G O. Near-infrared (NIR) spectroscopy. A new method for arthroscopic evaluation of low grade degenerated cartilage lesions. Results of a pilot study. BMC Musculoskelet Disord. 2007 May 29; 8:47.

Spahn G, Plettenberg H, Nagel H, Kahl E, Klinger H M, Muckley T, Günther M, Hofmann G O, Mollenhauer J A. Evaluation of cartilage defects with near-infrared spectroscopy (NIR): an ex vivo study. Med Eng Phys. 2008 April; 30(3):285-92.

Hofmann G O, Marticke J, Grossstück R, Hoffmann M, Lange M, Plettenberg H K, Braunschweig R, Schilling O, Kaden I, Spahn G. Detection and evaluation of initial cartilage pathology in man: A comparison between MRT, arthroscopy and near-infrared spectroscopy (NIR) in their relation to initial knee pain. Pathophysiology. 2010 February; 17(1):1-8.

Marticke J K, Hösselbarth A, Hoffmeier K L, Marintschev I, Otto S, Lange M, Plettenberg H K, Spahn G, Hofmann G O. How do visual, spectroscopic and biomechanical changes of cartilage correlate in osteoarthritic knee joints? Clin Biomech (Bristol, Avon). 2010 May; 25(4):332-40.

Spahn G, Klinger H M, Baums M, Hoffmann M, Plettenberg H, Kroker A, Hofmann G O. Near-infrared spectroscopy for arthroscopic evaluation of cartilage lesions: results of a blinded, prospective, interobserver study. Am J Sports Med. 2010 December; 38(12):2516-21.

Stumpfe S T, Pester J K, Steinert S, Marintschev I, Plettenberg H, Aurich M, Hofmann G O. Is there a correlation between biophotonical, biochemical, histological, and visual changes in the cartilage of osteoarthritic knee-joints? Muscles Ligaments Tendons J. 2013 Aug. 11; 3(3):157-65.

Spahn G, Plettenberg H, Hoffmann M, Klemm H T, Brochhausen-Delius C, Hofmann G O. The frequency of cartilage lesions in non-injured knees with symptomatic meniscus tears: results from an arthroscopic and NIR- (near-infrared) spectroscopic investigation. Arch Orthop Trauma Surg. 2017 June; 137(6):837-844.

Sarin J K, Te Moller N C, Mancini I A, Brommer H, Visser J, Malda J, van Weeren P R, Afara I O, Töyräs J. Arthroscopic near infrared spectroscopy enables simultaneous quantitative evaluation of articular cartilage and subchondral bone in vivo. Scientific reports. 2018 Sep. 7; 8(1):1-0.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. An arthroscopic probe device, comprising:
a probe shaft including a proximal end and probe tip positioned at a distal end, wherein the probe tip includes a bent portion at an angle in the range of about 50 to 150 degrees in relation to a central longitudinal axis of the probe shaft;
a handle including a proximal end and a distal end, wherein the distal end of the handle is connected to the proximal end of the probe shaft;
a cable including a first end and a second end, wherein the first end is connected to the proximal end of the handle;
at least one optical fiber, wherein a first end of the at least one optical fiber is optically connected to the probe tip, wherein the at least one optical fiber is positioned internally to the probe shaft, handle and cable, and wherein a second end of the at least one optical fiber terminates at the second end of the cable;

a prism positioned in the bent portion of the probe tip; and an optically transmissive spacer positioned in the probe tip, wherein the prism is positioned between the at least one optical fiber and the optically transmissive spacer, such that an optical path is created from the optical fiber through the spacer in the probe tip.

2. The device of claim 1, wherein the probe shaft is tapered from the proximal end to the distal end.

3. The device of claim 1, wherein the at least one optical fiber comprises one or more illumination optical fibers and one or more collection optical fibers.

4. The device of claim 1, wherein the at least one optical fiber comprises six illumination optical fibers and one collection optical fiber.

5. The device of claim 4, wherein the six illumination fibers are arranged annularly.

6. The device of claim 5, wherein the collection optical fiber is centrally positioned within the annular illumination fibers.

7. The device of claim 1, wherein the bent portion of the probe tip has a length in the range of about 0.1 mm to 10 mm.

8. The device of claim 1, wherein the first end of the at least one optical fiber directly contacts the prism.

9. The device of claim 1, wherein the optically transmissive spacer is a cylinder with a length in the range of 0.1 mm to 10 mm.

10. The device of claim 1, wherein the probe tip further includes an air gap, a vacuum cavity, a gaseous gap, or at least one second optical fiber positioned between the optically transmissive spacer and the prism.

11. The device of claim 1, wherein the optically transmissive spacer directly contacts the prism.

12. The device of claim 1, wherein the handle includes at least one groove, and the handle includes at least one orientation projection.

13. The device of claim 1, wherein the cable includes a bifurcation.

14. The device of claim 1, wherein the cable comprises an optical cable including optical connectors connected to the proximal end.

15. The device of claim 1, wherein the optical connectors comprise SubMiniature version A (SMA) connectors.

* * * * *